(12) United States Patent
Fulop et al.

(10) Patent No.: US 8,183,292 B2
(45) Date of Patent: May 22, 2012

(54) CHIRAL CYCLIC β-AMINO ACIDS AND THEIR DERIVATIVES, PHARMACEUTICAL COMPOSITIONS CONTAINING THEM AND THE USE OF SUCH COMPOUNDS

(75) Inventors: Ferenc Fulop, Szeged (HU); Zsolt Szakonyi, Szeged (HU)

(73) Assignee: BioBlocks Magyarorszag Gyogyszerkemiai es Fejleszto Kft., Budapest (HU)

( * ) Notice: Subject to any disclaimer, the term of this patent is extended or adjusted under 35 U.S.C. 154(b) by 242 days.

(21) Appl. No.: 12/513,369

(22) PCT Filed: Nov. 14, 2007

(86) PCT No.: PCT/HU2007/000107
§ 371 (c)(1),
(2), (4) Date: May 4, 2009

(87) PCT Pub. No.: WO2008/059299
PCT Pub. Date: May 22, 2008

(65) Prior Publication Data
US 2010/0081717 A1 Apr. 1, 2010

(30) Foreign Application Priority Data
Nov. 16, 2006 (HU) .................................... 0600847

(51) Int. Cl.
*A61K 31/17* (2006.01)
(52) U.S. Cl. ........................................ 514/580; 514/588
(58) Field of Classification Search .................. 514/580, 514/588
See application file for complete search history.

(56) References Cited

U.S. PATENT DOCUMENTS
2004/0010005 A1 1/2004 Barnett et al.

FOREIGN PATENT DOCUMENTS
WO 99/03822 * 1/1999

OTHER PUBLICATIONS

Duesberg et al., Drug Resistance Updates, 2007;10:51-58.*
International Search Report, dated Feb. 14, 2008, and Written Opinion of the International Searching Authority.
Zsolt Szakonyi et al., "Synthesis and transformations of enantiomeric 1,2-disubstituted monoterpene derivatives", Tetrahedron: Asymmetry, Nov. 17, 2000, pp. 4571-4579, vol. 11, No. 22, Elsevier Science Publishers, Amsterdam, the Netherlands.
Zsolt Szakonyi et al., "Mild and efficient ring opening of monoterpene-fused β-lactam enantiomers. Synthesis of novel β-amino acid derivatives", ARKIVOC, 2003, pp. 225-232, vol. XIV, XP-002466968.

* cited by examiner

Primary Examiner — San-Ming Hui
(74) Attorney, Agent, or Firm — Young & Thompson

(57) ABSTRACT

The invention relates to chiral cyclic β-amino acids of Formula (I) and their salts formed with pharmaceutically acceptable acids or bases, wherein the main meanings of the substituents are as follows: R stands for $C_{1-4}$ Alk; X stands for —COOH, —CONH$_2$, —CONH($C_{1-4}$ Alk), —CON($C_{1-4}$ Alk)$_2$, —COO($C_{1-4}$ Alk), —COPhe-O—($C_{1-4}$ Alk) or —CH$_2$OH; Y stands for —NH$_2$, —NHBoc, —NHFmoc, —NH($C_{1-4}$ Alk), —N($C_{1-4}$ Alk)$_2$, —NHCH$_2$Ph, or Ar—NH—C(=X$^0$)—N(R$^0$)— wherein Ar stands for a phenyl group substituted by $C_{1-4}$ alkoxy or halogen, X$^0$ stands for O or S, and R$^0$ stands for hydrogen or benzyl; and X+Y stands for —CONH— vagy —CON(Boc)-; with the proviso that when X stands for —COOH, then Y may be only different from —NH$_2$. The invention also relates to pharmaceutical compositions having multidrug-resistance reversing effect that contain one or more compound(s) of Formula (I) or a salt thereof and inert pharmaceutical carriers and/or auxiliary agents. The invention also relates to carboxylic acids of Formula (XX) and their salts.

11 Claims, 6 Drawing Sheets

Scheme 2

Scheme 3

Scheme 4

Scheme 5

Scheme 6

Scheme 7

Scheme 8

Scheme 9

Scheme 10

Scheme 11

Scheme 12

Explanation to schemes 9 to 12:

X = O, S; $R^1$ = H, $CH_2Ph$; $R^2$ = H, OMe; $R^3$ = H, OMe, Cl; n = 0, 2

Fig. 2

Summarizing Formula Table

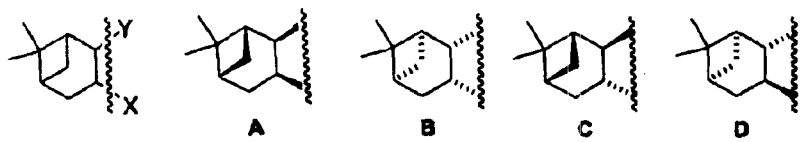

| Formula X, Y | A | B | C | D |
|---|---|---|---|---|
| X, Y = -CONH- | Example 1 (10) | Example 2 (33) | – | – |
| X, Y = -CONBoc- | Example 3 (11) | – | – | – |
| X = CONHMe<br>Y = NHBoc | Example 6 (12) | – | – | – |
| X = COOH<br>Y = NH$_2$ | Example 5 (13) | – | Example 30 (29) | – |
| X = COOMe<br>Y = NH$_2$.HCl | Example 6 (14) | – | – | – |
| X = COOEt<br>Y = NH$_2$.HCl | Example 7 (15) | Example 8 (34) | Example 23 (26) | Example 24 (39) |
| X = COOH<br>Y = NHBoc | Example 9 (16) | Example 10 (37) | Example 27 (31) | Example 28 (42) |
| X = COPhe-OEt<br>Y = NHBoc | Example 11 (17) | Example 12 (38) | Example 33 (32) | Example 34 (43) |
| X = COOH<br>Y = NHFmoc | Example 13 (18) | Example 14 (36) | Example 31 (30) | Example 32 (41) |
| X = COOH<br>Y = NMe$_2$.HCl | Example 15 (19) | – | – | – |
| X = COOEt<br>Y = NHCH$_2$Ph.HCl | Example 16 (20) | – | Example 25 (27) | – |

Fig. 2 Cont.

| Formula X, Y | A | B | C | D |
|---|---|---|---|---|
| X = COOH<br>Y = NHCH$_2$Ph.HCl | Example 17 (21) | – | – | – |
| X = CH$_2$OH<br>Y = NH$_2$.HCl | Example 18 (22) | Example 19 (35) | Example 29 (28) | Example 30 (40) |
| X = CH$_2$OH<br>Y = NHMe.HCl | Example 20 (23) | – | – | – |
| X = CH$_2$OH<br>Y = NHCH$_2$Ph.HCl | Example 21 (24) | – | – | – |
| X = CH$_2$OH<br>Y = NMe$_2$.HCl | Example 22 (25) | – | – | – |
| X = COOEt<br>Y = 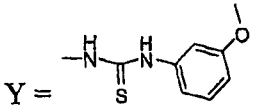 | Example 35 (44) | Example 36 (54) | Example 41 (49) | Example 42 (55) |
| X = COOEt<br>Y = 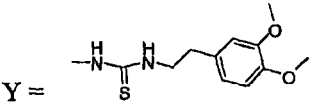 | Example 38 (46) | – | Example 45 (51) | – |
| X = COOEt<br>Y = 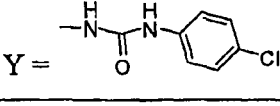 | Example 37 (45) | – | Example 43 (50) | Example 44 (56) |
| X = COOEt<br>Y = 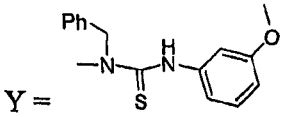 | Example 39 (47) | – | Example 46 (52) | – |
| X = COOEt<br>Y = 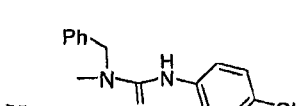 | Example 40 (48) | – | Example 47 (53) | – |

CHIRAL CYCLIC β-AMINO ACIDS AND THEIR DERIVATIVES, PHARMACEUTICAL COMPOSITIONS CONTAINING THEM AND THE USE OF SUCH COMPOUNDS

FIELD OF THE INVENTION

The invention relates to chiral cyclic β-amino acids and their derivatives, pharmaceutical compositions containing them and the use of such compounds.

BACKGROUND OF THE INVENTION

The systematic investigations concerning stereoisomeric alicyclic β-amino acids [F. Fülöp, *Chem. Rev.* 101, 2181-2204 (2001)] were considered for a long time as having only theoretical interest but about in the last decade it has turned out that several representatives of these compounds can be found in nature and have per se remarkable pharmacological effects and, resp., they are building elements of biologically active more complex compounds. The alicyclic β-amino acids play an important role even in the preparation of modified ("non-natural") analogues of biologically active peptides, and by changing the α-amino acids to β-amino acids it is possible to modify the effect of the peptide and/or its stability can be increased.

Due to the occurrence in nature of the alicyclic β-amino acids and such acids of other types as well as the valuable biological activity of their derivatives and their manifold synthetic useability, several novel enantioselective processes have been elaborated for their synthesis [F. Fülöp, *Chem. Rev.* 101, 2181-2204 (2001); F. Fülöp, T. A. Martinek and G. K. Tóth, *Chem. Soc. Rev.* 35, 323-334 (2006)]. This can be followed in the preparation of β-amino acid enantiomers and their use of ever increasing degree in asymmetric reactions.

A novel direction in the preparation of chiral β-amino acids is the β-amino acid synthesis from chiral monoterpene derivatives [e.g. from (+)- and (−)-α-pinene, (+)-3-carene] [Z. Szakonyi, T. Martinek, A. Hetényi and F. Fülöp, *Tetrahedron: Asymmetry,* 11, 4571-4579 (2000); S. Gyónfalvi, Z. Szakonyi and F. Fülöp: *Tetrahedron:Asymmetry,* 14, 3965-3972 (2003)]. From the thus-obtained β-amino acid derivatives having monoterpene skeleton 1,3-heterocyclics of varied structures have been prepared [Z. Szakonyi, T. Martinek, A. Hetényi and F. Fülöp, *Tetrahedron:Asymmetry,* 11 4571-4579 (2000); S. Gyónfalvi, Z. Szakonyi and F. Fülöp, *Tetrahedron: Asymmetry,* 14, 3965-3972 (2003); Z. Szakonyi and F. Fülöp, *Arkivoc,* xiv, 225-232 (2003)].

It has been observed, however, that, due to the monoterpene skeleton wherein the amino group of the amino acid is attached to a tertiary carbon atom, the reactivity of the compounds in relation to the reactivity of the simpler alicyclic analogues is decreased in a high degree. However, by the suitable choice of the starting materials the amino group can be attached to the secondary carbon atom whereby the β-amino acid derivatives get normal reactivity, simultaneously preserving the enantiomeric purity secured by the natural monoterpene starting materials.

It is known that most of the cancer patients have to be treated with chemotherapeutical agents, too. However, the effectivity of the chemotherapy is strongly decreased by the appearance of resistance against cytostatica, especially the multidrug resistance (MDR) against chemotherapeutical drugs. The resistance against the anti-cancerous drugs is often transmitted by the expression of excessive degree of the membrane pump called P-glycoprotein (P-gp or MDR1), and this protein is coded by a gene called mdr1.

The P-gp is a member of the ABC superfamily. These transporters depending on ATP decrease the intracellular drug concentration below the cytotoxic levels, whereby the cytostatica become increasingly less effective and the toxic side-effects become increasingly stronger during the treatment, since the membrane pump transports the cytostatica from the intracellular space to the extracellular space. The strong decrease of the intracellular cytostaticum concentration during the treatment renders possible the survival and metastasis of the pathogenic tumour cells [E. Andicott et al., *Ann. Rev. Bioch.* 58, 137-171 (1989)].

Consequently, the surmounting of the multidrug resistance is extremely important since in this way numerous cancers and contagious illnesses can be successfully treated. Today no effective drug is known by the aid of which this aim could be attained in vivo.

The investigation of multidrug resistance gains ground in an increasingly wide sphere. A very promising method of surmounting MDR is to develop MDR-modulators which can inhibit the activity of the P-glycoprotein.

SUMMARY OF THE INVENTION

Surprisingly it has been found that the novel terpene derivatives according to the invention are biologically active, non-toxic compounds which can surmount in a very low concentration the resistance against chemotherapeutical drugs of the pathological tumour cells and inhibit the pump activity of the pathological MDR tumour cells.

Based on the above, the invention relates to chiral 2-amino-6,6-dimethylbicyclo[3.1.1]heptane-3-carboxylic acid derivatives of general formula (I)—

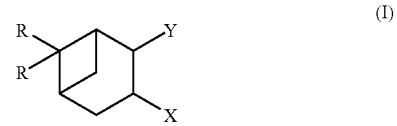

wherein
R stands for $C_{1-4}$ Alk;
X stands for —COOH, —CONH$_2$, —CONH($C_{1-4}$ Alk), —CON($C_{1-4}$ Alk)$_2$, —COO($C_{1-4}$ Alk), —COPhe-O—($C_{1-4}$ Alk) or —CH$_2$OH;
Y stands for —NH$_2$, —NHBoc, —NHFmoc, —NH($C_{1-4}$ Alk), —N($C_{1-4}$Alk)$_2$, —NHCH$_2$Ph, or) Ar-NH—C(=X$^0$)—N(R$^0$)— wherein Ar stands for a phenyl group substituted by one or two $C_{1-4}$ alkoxy group(s) or by one halogen, X$^0$ stands for O or S, and R$^0$ stands for hydrogen or benzyl; and
X+Y stands for —CONH— vagy —CON(Boc)-; with the proviso that when X stands for —COOH, then Y may be only different from —NH$_2$— and to their salts formed with pharmaceutically acceptable acids or bases.

In the formulas Boc stands for tert-butoxycarbonyl, Alk stands for alkyl, Hlg stands for halogen, Fmoc stands for fluorenyl-methoxycarbonyl, Phe stands for phenylalanine and Me stands for methyl.

It is very surprising that the compounds according to the invention induce the chemical sensitisation of the resistant Mdr-tumour cells and suppress their efflux-pump activity. That results in so high values of the intracellular chemotherapeutics concentration that no difference can be observed in relation to the parenteral cells.

Consequently, the compounds according to the invention are biologically active and suppress the efflux-pump activity of malignant MDR-tumour cells even at very low concentrations. They are not toxic in vivo even at higher concentrations. They are active immediately after the contact with the cells. Thus, the compounds according to the invention enhance in the first line the chemotherapeutic efficiency, that is, they can be used in the chemotherapy with other active agents too.

BRIEF DESCRIPTION OF THE DRAWINGS

FIG. 2 depicts the Summarizing Formula Table.

DETAILED DESCRIPTION OF THE INVENTION

Figure 1:
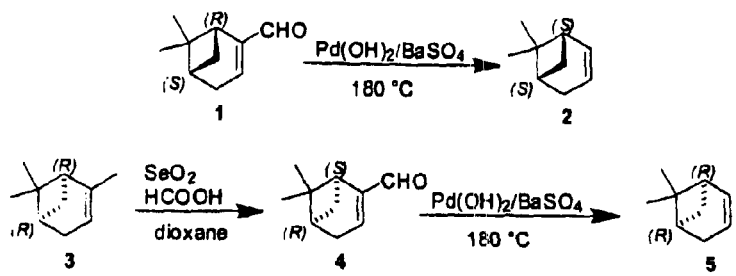
FIG. 1 depicts reaction schemes 2 to 12.
Figure 1:
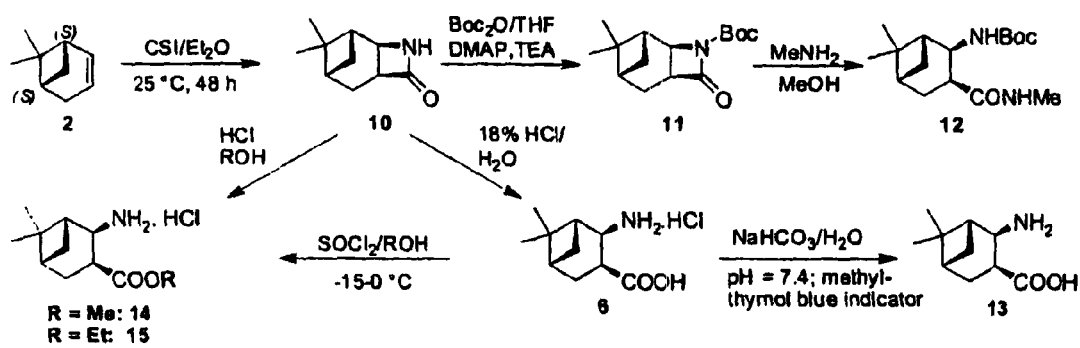
Figure 1:
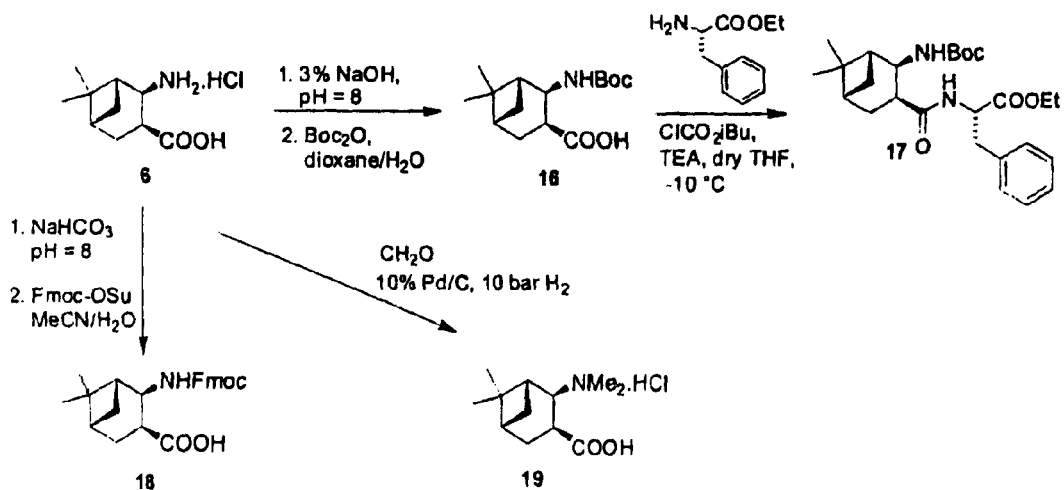
Figure 1:
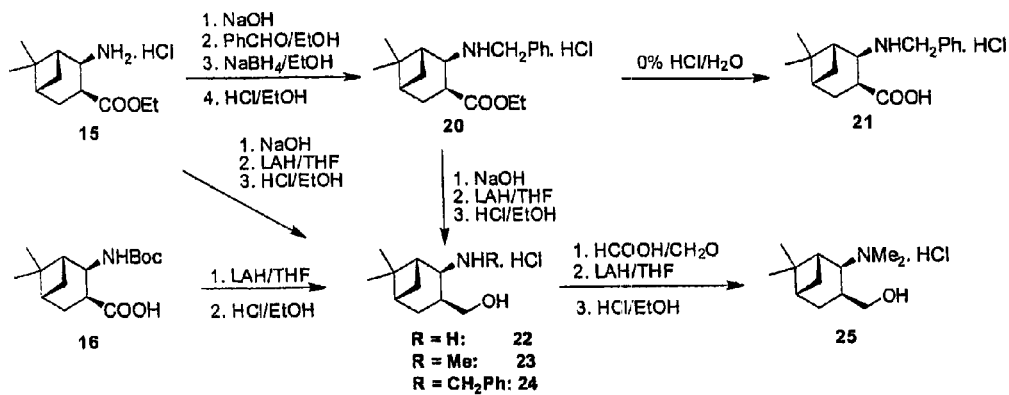
Figure 1:
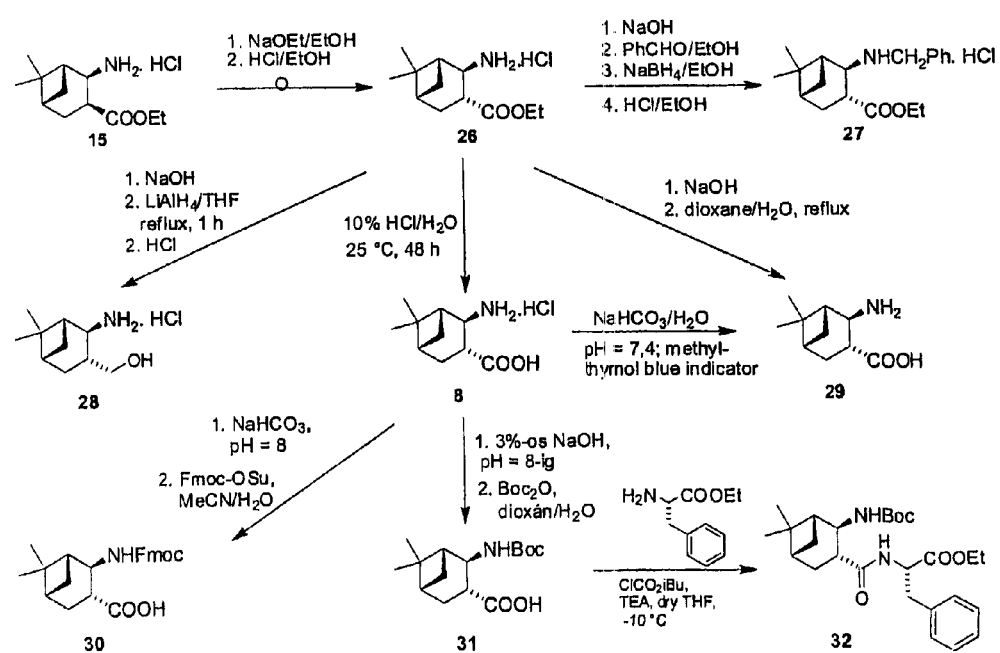
Figure 1:
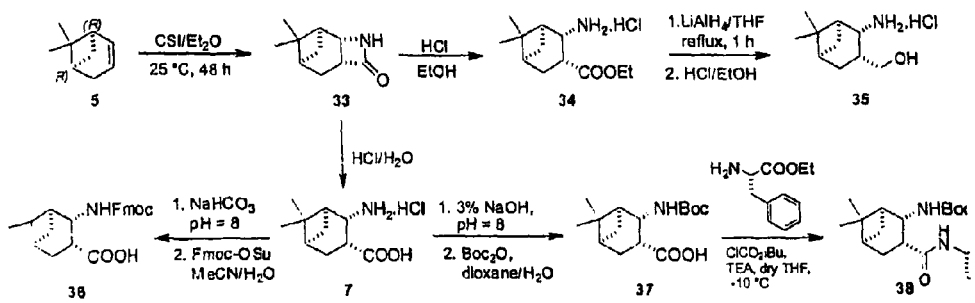
Figure 1:
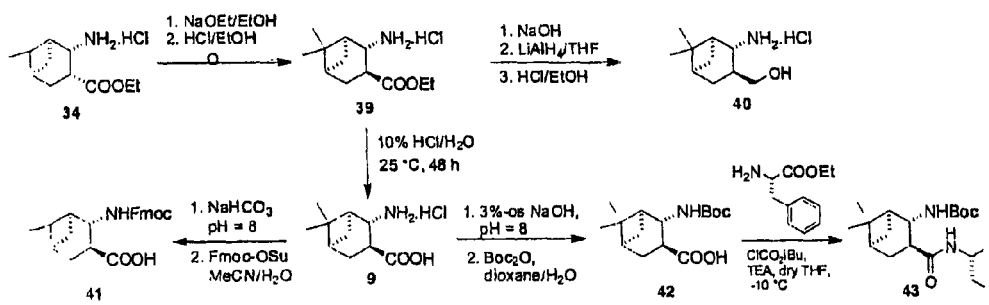
Figure 1:
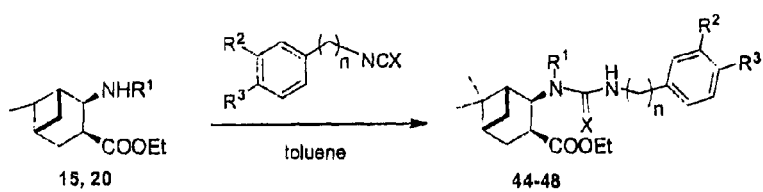
Figure 1:
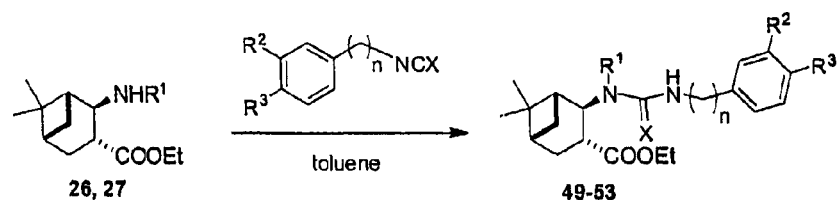
Figure 1:
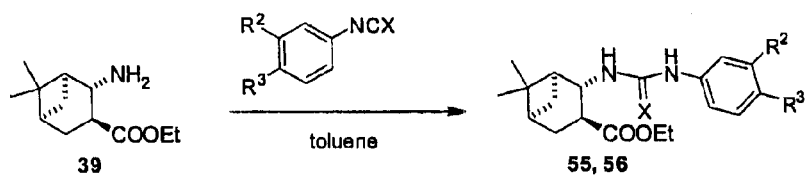
Figure 1:
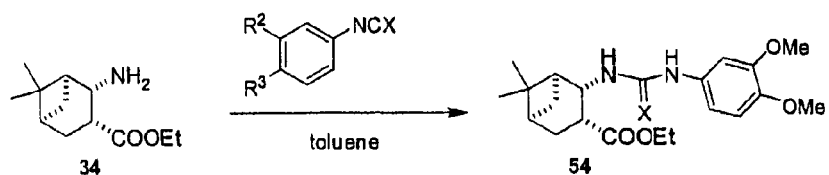

The following compounds according to the invention have shown especially advantageous effects:

(1R,2R,5S,7R)-N-tert-butoxycarbonyl-8,8-dimethyl-3-azatricyclo-[5.1.1.0$^{2,5}$]nonane-4-one (compound of formula 11), (1R,2R,3R,5R)-2-(9H-fluoren-9-yl-methoxycarbonylamino)-6,6-dimethyl-bicyclo[3.1.1]heptane-3-carboxylic acid (compound of formula 30), (1R,2R,3S,5R)-1-(3-ethoxycarbonyl-6,6-dimethyl-bicyclo-[3.1.1]heptane-2-yl)-3-(3-methoxyphenyl)-thiourea (compound of formula 44), (1R,2R,3S,5R)-1-(3-ethoxycarbonyl-6,6-dimethyl-bicyclo[3.1.1]heptane-2-yl)-3-(3,4-dimethoxy-phenylethyl)-thiourea (compound of formula 46), (1R,2R,3S,5R)-1-benzyl-1-(3-ethoxycarbonyl-6,6-dimethyl-bicyclo[3.1.1]heptane-2-yl)-3-(3-methoxyphenyl)-thiourea (compound of formula 47), (1R,2R,3R,5R)-1-(3-ethoxycarbonyl-6,6-dimethyl-bicyclo[3.1.1]heptane-2-yl)-3-(3-methoxyphenyl)-thiourea (compound of formula 49), (1R,2R,3R,5R)-1-(3-ethoxycarbonyl-6,6-dimethyl-bicyclo[3.1.1]heptane-2-yl)-3-(4-chlorophenyl)-urea (compound of formula 50), (1R,2R,3R,5R)-1-(3-ethoxycarbonyl-6,6-dimethyl-bicyclo[3.1.1]heptane-2-yl)-3-(3,4-dimethoxyphenylethyl)-thiourea (compound of formula 51), (1R,2R,3R,5R)-1-benzyl-1-(3-ethoxycarbonyl-6,6-dimethyl-bicyclo[3.1.1]heptane-2-yl)-3-(3-methoxyphenyl)-thiourea (compound of formula 52), and (1S,2S,3S,5S)-1-(3-ethoxycarbonil-6,6-dimethyl-bicyclo[3.1.1]heptane-2-yl)-3-(4-chlorophenyl)-urea (compound of formula 56).

The invention also relates to the preparation of the compounds of general formula (I). The process according to the invention can be realized according to the enclosed reaction scheme 1 wherein the meanings of the symbols and abbreviations, resp., are as follows:

R$^1$=alkyl
R$^2$=alkyl or aralkyl
R$^3$=alkyl
R$^4$=alkyl, aralkyl or aryl
R$^5$=alkyl
R$^6$=H, alkyl, aralkyl or aryl
P=N-protecting group (e.g. Boc, Fmoc, etc.)
X$^1$=activating group (e.g. halogen, acid residue)
Y$^1$=O or S
CSI=chlorosulphonyl isocyanate
LAH=lithium aluminium hydride
TEA=triethyl amine
THF=tetrahydrofuran.

For preparing the compounds according to the invention one proceeds as follows:

β-lactam enantiomers are prepared by reacting suitable monoterpenes with chlorosulphonyl isocyanate and then treating the intermediary product with an alkali;

the amino group of the thus-obtained compounds is preferably protected with an alkoxycarbonyl group, then N-protected acid amides are prepared by aminolysis of the β-lactam ring of the thus-obtained compound;

by carrying out the acid solvolysis of the β-lactams with inorganic acids in water cis-amino acids, whereas by carrying out the solvolysis in suitable alcohols (R$_3$—OH) esters are directly prepared;

trans-amino acid esters are prepared by the alkaline isomerisation of the cis-amino acid esters, and by the hydrolysis of the esters the corresponding trans-amino acids are prepared;

N-substituted amino acid esters are prepared by the reductive alkylation of amino acid esters, and by hydrolysis of the thus-obtained compounds the corresponding N-substituted amino acids are prepared;

the amino group of the amino acids is protected preferably with an alkoxycarbonyl group, and the thus-obtained N-protected amino acids are coupled preferably by the mixed anhydride method with other amino acids and amino acid esters, resp., whereby dipeptides are prepared;

by reducing the amino acid esters preferably with inorganic hydrides amino alcohols are prepared, and by carrying out the reduction with alkyl- or aryl-isocyanates and, resp., -isothiocyanates urea and, resp., thiourea derivatives are prepared.

The β-lactam enantiomers exist only in 1,2-cis diastereomeric form, whereas the compounds obtained therefrom also exist in 1,2-cis and 1,2-trans diastereomeric forms. The compound series cis can be prepared directly from the β-lactam enantiomers, while the trans series can be obtained by the alkaline epimerisation of the cis-amino acid ester (see Example 23).

The concrete methods for preparing the compounds according to the invention are described, based on reaction schemes 3-12, in Examples 1-47.

The reactions can be followed by thin-layer chromatography. The processing up can be carried out by evaporation or extraction. The product can be purified by crystallization or chromatography. The structure and purity of the compounds can be proved and checked, resp., by NMR spectroscopy, measuring the melting point and/or CHN microanalysis.

The invention also relates to multidrug resistance reversing pharmaceutical compositions containing compounds of general formula (I) or their salts. In compliance with the invention these compositions can be prepared as follows: one or more compound(s) of general formula (I) or the salts thereof is/are mixed with usual inert pharmaceutical carriers and/or auxiliary agents, whereby MDR-reversing pharmaceutical compositions are obtained.

Furthermore, the invention also relates to the use of the compounds of general formula (I) and/or the salts of such compounds for preparing pharmaceutical compositions reversing multidrug resistance.

The scope of the invention also relates to the novel 2-amino-6,6-dimethyl-bicyclo [3.1.1]heptane-3-carboxylic acids and their salts formed with pharmaceutically acceptable acids and bases, resp., obtained as intermediary products when preparing the novel compounds of general formula (I). The preparation of the compounds of formulas 6, 7, 8, and 9 is described in Examples 5, 10, 26.b), and 28, resp.

The compounds according to the invention can be transformed with physiologically acceptable acids and bases, resp., to salts. Inorganic or organic acids of this kind are the hydrochloric acid, hydrobromic acid, phosphoric acid, formic acid, acetic acid, propionic acid, glycolic acid, lactic acid, citric acid, maleic acid, fumaric acid, anthranilic acid, methansulphonic acid, naphthalenesulfonic acid, sulfanilic acid, and cinnamic acid.

Sodium hydroxide, potassium hydroxide, and calcium hydroxide are mentioned as specifically acceptable bases.

In the practice the compounds according to the invention of general formula (I) can be administered in solid, liquid or spray form alone or together with one or more usual pharmaceutical carrier(s) or auxiliary agent(s). Accordingly, the invention also relates to pharmaceutical compositions that contain an effective amount of the compounds of general formula (I) together with a pharmaceutically acceptable carrier. As a matter of course, the compounds according to the invention can also be administered together with other MDR-reversing compounds.

As solid carriers that can be used in the compositions according to the invention one or more material(s) can be used which simultaneously serve as sliding agent, solubilizing agent, suspending agent, binder, filler, pressing agent, disintegrating agent, flavouring agent or capsulating agents.

In the case of powders the carrier can be a finely divided solid material that is mixed with finely divided particles of the compounds of general formula (I). In the case of tablets, the compound of general formula (I) is mixed in a suitable ratio with a carrier which has the required pressing properties, and the mixture is pressed to the desired form and size.

The above-mentioned powders and tablets contain the compound of general formula (I) in an amount ranging up to 99% by mass.

The compositions of spray form are generally used as aerosol compositions for absorption on the skin surface or through the lungs.

As examples of the solid carriers which can be used in the compositions according to the invention the following are mentioned by way of example: talc, calcium phosphate, magnesium stearate, lactose, dextrin, starch, gelatine, cellulose, methyl cellulose, sodium carboxymethylcellulose, polyvinyl pyrrolidone and waxes of low melting point.

In the compositions according to the invention any pharmaceutically acceptable liquid carrier can be used which is suitable for preparing solutions, suspensions, emulsions, syrups and therapeutic drinks. The compounds of formula (I) can be dissolved or suspended in a pharmaceutically acceptable liquid carrier such as water, organic solvents or pharmaceutically acceptable oils or fats or a mixture thereof. The liquid compositions may contain other suitable pharmaceutical additives such as solubilising agents, emulgators, buffers, conserving agents, sweeteners, flavouring agents, suspending agents, thickeners, colouring agents, viscosity regulators, stabilizers, osmotic pressure regulators, and similar agents.

For oral or parenteral administration the following examples of liquid carriers are mentioned: water, aqueous solutions containing additives such as cellulose derivatives, preferably sodium carboxymethylcellulose, alcohols including primary and secondary alcohols such as glycols, alcohol derivatives or oils such as fractionated coconut oil and arachis oil. In case of parenteral administration the carrier oil can be an ester such as ethyl oleate or isopropyl myristate.

The orally administrable compositions according to the invention can be liquid or solid.

The compositions according to the invention that are sterile solutions or suspensions can be used as intramuscular, intraperitoneal or subcutaneous injections. The sterile solutions can be administered intravenous too.

The compounds according to the invention can be formulated together with pharmaceutically effective other materials. The selection of such materials depends on the aim of using the compositions.

In the compositions the concentration of the compounds of general formula (I) depends on several factors such as the method of administration, the chemical nature of the compounds, the state and clinical indication of the patient. Therefore, the concentration can vary in a wide range. Generally the concentration of the active agent can be 0.002-99% by mass, e.g. 0.01-70% by mass, preferably 0.05-40% by mass, more preferably 0.1-20% by mass.

The compositions according to the invention can be administered enterally, parenterally, locally, rectally or systemically depending on the prescription and the active agent used, e.g. in the form of tablets, capsules, powder, granules, syrup, spray, or injection solution.

The compositions for enteral administration can be e.g. powders, simple or coated tablets, tablets with protracted effect, soft capsules, hard capsules, rectal suppositories, suspensions and solutions which, if desired, may contain the active agents together with one or more usual carriers.

The compositions for parenteral administration can be e.g. preparations for intradermal, subcutaneous, intraperitoneal or intravenous injections or infusions. Other parenteral compositions can be applied not only on the skin but also on the mucous membrane. Such local compositions can be e.g. gels, creams, ointments, shampoos, soaps, sprays, rinsing agents, smears, aerosols, and other pharmaceutical preparations suitable for local administration.

The compounds according the inventions preserve their effect when used in any form, e.g. when used in the usual oral or rectal or injection form.

In the case of oral administration the daily dose of the compounds according to the invention amounts in adults to 200-1000 mg, preferably 50-500 mg, more preferably 20-100 mg. These doses can be increased or decreased depending on the state of the patients.

The toxic effect of the compounds was measured on MRC-5 human fibroblast cell lines in accordance with the method that has been described in the article published by Molnár et al. [L. Molnár, G. M. Keserü, Á. Papp, Z. Lörincz, G. Ambrus és F. Darvas.: A neural network based classification scheme for cytotoxicity predictions: Validation on 30,000 compounds, *Bioorg. Med. Chem. Lett.* 16(4), 1037-9 (2006)]. The cells were incubated for a cell cycle (24 hours) with solutions of various concentrations prepared from the compounds, in the presence of 1% of DMSO. 3 parallel measurements were carried out with 6 different concentrations. The ratio of the viable cells was determined by reducing the Alamaar Blue (resazurine) reagent that was followed fluorimetrically. The measured materials were not toxic on the given cell line in a concentration of 128 µmol after incubation for one day.

In the following Table 1 the cytotoxicity of some compounds according to the invention is given.

TABLE 1

| Number of the compound formula | Survival (%) [c = 128 µM] |
|---|---|
| 38 | 125.3 |
| 44 | 128.1 |
| 45 | 176.7 |

TABLE 1-continued

| Number of the compound formula | Survival (%) [c = 128 μM] |
|---|---|
| 46 | 182.2 |
| 47 | 97.7 |
| 49 | 250.9 |
| 50 | 167.6 |
| 52 | 113.0 |
| 55 | 214.1 |
| 56 | 116.8 |

The preparation of the starting compounds (1S,5S)- and (1R,5R)-apopinene (2 and 5) used for the synthesis of the compounds according to the invention was carried out in compliance with the literature method, in the way as represented on the enclosed reaction scheme 2 [Shibuya K., *Synth. Commun.*, 24, 2923-2941 (1994); Lightner D. A.; Crist, B. V. *Tetrahedron*, 41, 3021-3028 (1985)]. The (−)-(1R,5S)-myrtenale (1) and the (+)-(1R,5R)-α-pinene (3) are commercially available products (Sigma-Aldrich Kft.).

Reaction schemes 3-12 show the synthesis of the compounds according to the invention. The detailed description of the experiments and the physical and chemical characteristics of the compounds prepared are given in the individual Examples.

Schemes 2 to 12 are illustrated in FIG. 1 in the enclosed drawing.

Experimental Section

General Procedures. $^1$H NMR spectra were recorded on a Bruker Avance DRX 400 spectrometer [400.13 MHz ($^1$H) and 100.61 MHz ($^{13}$C), δ=0 (TMS)] in CDCl$_3$ or in D$_2$O in a 5 mm tube. Chemical shifts are expressed in ppm (δ) relative to TMS as internal reference. J values are given in Hz.

The enantiomer purity of the reveal compounds were performed by GC measurements on a Chrompack CP-9002 system, consisting of a 901A Flame Ionization Detector and a Maestro II Chromatography data system (Chrompack International B.V., Middelburg, The Netherlands). The column used for direct separation of the enantiomers was a CHIRASIL-DEX CB column (2500×0.25 mm I.D.) at 170° C., 80 kPa for azetidinones and 100° C., 25 kPa for apopinene. Optical rotations were obtained with a Perkin-Elmer 341 polarimeter. FT-IR spectra were recorded on a Perkin-Elmer model 1000 spectrophotometer. Microanalyses were determined on a Perkin-Elmer 2400 elemental analyser. Melting points were determined on a Kofler apparatus and are uncorrected.

Example 1

(1R,2R,5S,7R)-8,8-Dimethyl-3-Azatricyclo[5.1.1.0$^{2,5}$]Nonan-4-One (Compound 10) (Scheme 3)

A mixture of 12.21 g (100.0 mmol) of (−)-(1S,5S)-apopinene (2), prepared via literature method [Lightner, D. A.; Crist, B. V. *Tetrahedron*, 41, 3021-3028 (1985)], and 14.30 g (101.2 mmol) of chlorosulfonyl isocyanate (CSI) was stirred in 300 ml of dry diethyl ether for 48 h at room temperature. 20.4 g (162 mmol) of dry sodium sulfite in 140 ml water was then cautiously added dropwise to the solution. The pH was held at 7-8 by the addition of 20% aqueous potassium hydroxide. After 2 h stirring at the appropriate pH, the organic phase was separated and the aqueous layer was extracted with diethyl ether (2×100 ml). The combined organic layer was dried (Na$_2$SO$_4$) and evaporated, and the white crystalline product obtained was recrystallized from n-hexane.

Isolated compound: 13.54 g (82%); mp: 68-72° C.; $[α]_D^{20}$=−80.0 (c=0.5, MeOH; ee>99%); IR=3247, 2914, 1710, 1380, 1256, 1189 cm$^{-1}$. Anal. Calcd. for C$_{10}$H$_{15}$NO (165.23): C, 72.69; H, 9.15; N, 8.48; Found: C, 72.52; H, 9.27; N, 8.31. $^1$H NMR (CDCl$_3$) δ (ppm): 0.88 (3H, s, Me-8), 1.30 (3H, s, Me-8), 1.50 (1H, d, H-9, J=11.1 Hz), 1.82-1.98 (2H, m,), 2.07-2.29 (3H, m,), 3.28 (1H, dd, H-5, J=10.32 Hz), 3.95-4.00 (1H, m), 5.87 (1H, s, NH); $^{13}$C NMR (CDCl$_3$) δ (ppm): 19.7 (Me-6), 23.3 (CH$_2$), 24.7 (CH$_2$), 26.8 (Me-6), 40.0 (C$_q$), 41.9 (CH), 43.7 (CH), 44.9 (CHC=O), 51.8 (CHN), 173.9 (C=O).

Example 2

(1S,2S,5R,7S)-8,8-Dimethyl-3-Azatricyclo[5.1.1.0$^{2,5}$]Nonan-4-One (Compound 33) (Scheme 7)

The synthesis of 1S,2S,5R,7S enantiomer 33 was accomplished by analogy with Example 1, starting from (+)-(1R,5R)-apopinene 5 which was prepared via literature method [Lightner, D. A.; Crist, B. V. *Tetrahedron*, 41, 3021-3028 (1985)]; $[α]_D^2$=+61.5 (c=0.5, MeOH; ee=90%); all the spectroscopic data and mp were similar to those for (−)-enantiomer 10.

Example 3

(1R,2R,5S,7R)-N-tert-Butoxycarbonyl-8,8-Dimethyl-3-Azatricyclo[5.1.1.0$^{2,5}$]-Nonan-4-One (Compound 11) (Scheme 3)

To a stirred solution of 0.30 g (1.8 mmol) of (1R,2R,5S,7R)-8,8-dimethyl-3-azatricyclo[5.1.1.0$^{2,5}$]nonan-4-one (10) prepared according to Example 1, and dry THF (10 ml), triethylamine (0.47 g, 4.6 mmol), di-tert-butyl dicarbonate (0.51 g, 2.3 mmol) and a catalytic amount of 4-dimethylaminopyridine were added while stiffing. After stirring for 6 h at room temperature (the reaction was monitored by means of TLC), the mixture was evaporated to dryness. The oily residue obtained was purified by flash chromatography on a silica gel column (n-hexane:ethyl acetate=9:1), resulting in a white crystalline product (0.43 g, 89%): mp: 64-66° C.; $[α]_D^{20}$=−41.1 (c=0.5, MeOH); IR=2926, 1803, 1707, 1349, 1156 cm$^{-1}$. Anal. Calcd. for C$_{15}$H$_{23}$NO$_3$ (265.35): C, 67.90; H, 8.74; N, 5.28. Found: C, 68.16; H, 8.54; N, 5.35. $^1$H NMR (CDCl$_3$) δ (ppm): 0.89 (3H, s), 1.31 0.89 (3H, s), 1.35 (1H, d, J=11.6 Hz, H-9), 1.50 (9H, s), 1.81-2.00 (2H, m, H-6, H-7), 2.14-2.25 (2H, m, H-6, H-9), 2.51-2.57 (1H, m, H-1), 3.29 (1H, dd, J=10.3, 6.2 Hz, H-2), 4.27 (1H, dd, J=5.6, 4.0 Hz, H-5). $^{13}$C NMR (CDCl$_3$) δ (ppm): 20.5 (Me), 24.3 (C-9), 25.5 (C-6), 27.3 (Me), 28.7 (Me$_3$C), 39.8 (C-8), 42.1, 42.5, 44.1, 55.5, 83.4 (Me$_3$C), 148.6 (C-4), 170.5 (Me$_3$COC=O).

Example 4 tert-Butyl (1R,2R,3S,5R)-(2-Methylaminocarbonyl-6,6-Dimethylbicyclo[3.1.1]-Hept-3-yl)Carbamate (Compound 12) (Scheme 3)

0.29 g (1.08 mmol) of the (1R,2R,5S,7R) N-Boc β-lactam (11), prepared according to Example 3, was dissolved in a 25% solution of methylamine in dry methanol (50 ml). The reaction mixture was allowed to stand at 4° C. for 12 h. After evaporation to dryness, the yellow crude product was purified by flash chromatography on a silica gel column (n-hexane: ethyl acetate=4:1) to give 12 as white crystals.

Isolated compound: 0.28 g (86%): mp: 104-105° C.; $[\alpha]_D^2$=+52.7 (c=0.5, MeOH); IR=3330, 2979, 1668, 1539, 1179. Anal. Calcd. for $C_{16}H_{28}N_2O_3$ (296.41): C, 64.83; H, 9.52; N, 9.45. Found: C, 64.97; H, 10.05; N, 9.23. $^1$H NMR (CDCl$_3$) δ (ppm): 0.89 (3H, s, Me-6), 1.01 (3H, s, Me-7), 1.22 (3H, s, Me-6), 1.41 (9H, s), 1.31 (1H, d, J=10.1 HZ), 1.74-1.96 (3H, m), 2.12-2.28 (2H, m), 2.77 (3H, d, J=5.0 Hz, NHMe), 3.02 (1H, dt, J=10.1, 3.5 Hz, H-3), 4.33 (1H, t, J=9.7 Hz, H-2), 5.04 (1H, d, J=9.7 Hz, NHMe), 5.73 (1H, br s, NHBoc). $^{13}$C NMR (CDCl$_3$) δ (ppm): 21.0 (Me), 25.4 (CH$_2$), 26.8 (Me), 27.3 (CH), 28.8 (CH$_2$), 29.0 (3×Me), 39.7 (C$_q$), 40.0 (CH), 41.0 (CH), 46.8 (CH), 49.8 (CH), 79.8 (CMe$_3$), 156.6, 176.1.

Example 5

(1R,2R,3S,5R)-2-Amino-6,6-Dimethylbicyclo[3.1.1] Heptan-3-Carboxylic Acid (Compound 13) (Scheme 3)

0.50 g (3.0 mmol) of (1R,2R,5S,7R)-8,8-dimethyl-3-azatricyclo[5.1.1.0$^{2,5}$]nonan-4-one (10), prepared according to Example 1, was stirred in a solution of 5 ml of 15% hydrochloric acid at room temperature. When the mixture became clear (approx. 1 h), the solution was evaporated to dryness and the resulted white crystalline product was washed with acetone and filtered off. 0.61 g (94%) of (1R,2R,3S,5R)-2-amino-6,6-dimethyl-bicyclo[3.1.1]heptan-3-carboxylic acid hydrochloride (6) was isolated by this method; mp: 248-249° C.; $[\alpha]_D^{20}$=+22.5 (c=0.5, MeOH; ee>99%); IR=2904, 1724, 1584, 1489, 1175 cm$^{-1}$. Anal. Calcd. for $C_{10}H_{18}ClNO_2$ (219.71): C, 54.67; H, 8.26; N, 6.38. Found: C, 54.87; H, 8.02; N, 6.71. $^1$H NMR (D$_2$O) δ (ppm): 0.89 (3H, s, Me-6), 1.27 (3H, s, Me-6), 1.48 (1H, d, J=11.1 Hz), 2.04-2.16 (2H, m), 2.31-2.39 (2H, m) 3.39 (1H, dt, J=10.7, 3.6 Hz), 3.98 (1H, d, J=9.6 Hz). $^{13}$C NMR (CDCl$_3$) δ (ppm): 19.7 (Me), 24.3 (CH$_2$), 25.8 (Me), 29.4 (CH$_2$), 34.4 (CH), 39.3 (C$_q$), 39.6 (CH), 44.2 (CH), 50.2 (CH), 178.5 (C=O).

The (1R,2R,3S,5R)-2-amino-6,6-dimethylbicyclo[3.1.1] heptan-3-carboxylic acid hydrochloride (6) prepared above, was dissolved in 5 ml of water and the pH of the solution was adjusted to pH=7.4 with 10% solution of NaHCO$_3$ under ice cooling in the presence of methylthymol blue indicator. After 1 h stirring at 0° C. the precipitated product 13 was filtered and washed with a small amount of ice-cold distilled water.

Isolated compound: 0.29 g (58%); mp: 270° C.; $[\alpha]_D^{20}$=-1.6 (c=0.50, MeOH); IR=3243, 2972, 1625, 1576, 1474, 1382 cm$^{-1}$. Anal. Calcd. for $C_{10}H_{17}NO_2$ (183.25): C, 65.54; H, 9.35; N, 7.64. Found: C, 65.48; H, 9.57; N, 7.42. $^1$H NMR (CD$_3$OD) δ (ppm): 0.99 (3H, s), 1.36 (3H, s), 1.73 (1H, d, H-4, J=10.6 Hz), 2.00-2.06 (1H, m,), 2.12 (1H, dt, J=2.0, 5.5 Hz), 2.26-2.39 (3H, m), 3.02 (1H, dt, J=9.6, 4.5 Hz), 3.82 (1H, dt, J=9.6, 2.0 Hz). $^{13}$C NMR (CDCl$_3$) δ (ppm): 22.9 (Me), 26.1 (CH$_2$), 27.6 (Me), 32.5 (CH$_2$), 37.8 (CH), 39.3 (C$_q$), 42.3 (CH), 47.2 (CH), 52.0 (CH), 183.1 (C=O).

Example 6

Methyl (1R,2R,3S,5R)-2-Amino-6,6-Dimethylbicyclo[3.1.1]Heptan-3-Carboxylate Hydrochloride (Compound 14) (Scheme 3)

Compound 14 was prepared by two methods:
Method 6a
2.0 g (12.1 mmol) of (1R,2R,5S,7R)-8,8-dimethyl-3-azatricyclo[5.1.1.0$^{2,5}$]nonan-4-one (10), prepared according to Example 1, was stirred in solution of 10% hydrochloric acid in dry methanol (20 ml) at room temperature. After 1.5 h stirring, the solution was evaporated to dryness and the resulted crystalline product was recrystallized from isopropyl ether/ethyl acetate mixture.

Isolated compound: 1.98 g (71%); mp: 157-160° C.; $[\alpha]_D^{20}$=+4.8 (c=0.5, MeOH); IR=2926, 1724, 1498, 1205 cm$^{-1}$. Anal. Calcd. for $C_{11}H_{20}ClNO_2$ (233.74): C, 56.52; H, 8.62; N, 5.99. Found: C, 56.73; H, 9.01; N, 6.17. $^1$H NMR (CDCl$_3$) δ (ppm): 0.97 (3H, s, Me-6), 1.35 (3H, s, Me-6), 1.54 (1H, d, H-4, J=11.1 Hz), 2.08-2.22 (3H, m,), 2.36-2.45 (1H, m), 3.54 (1H, dt, J=10.1, 3.5 Hz), 3.84 (3H, s, COOMe), 4.09 (1H, d, J=10.1 Hz). $^{13}$C NMR (CDCl$_3$) δ (ppm): 19.2, 25.3, 28.5, 38.7, 39.0, 43.6, 44.1, 47.8, 49.9, 53.1, 176.7.

Method 6b
0.31 ml (4.57 mmol) of thionyl chloride was added dropwise with stirring to 4 ml of dry methanol keeping the internal temperature below −12° C. during the addition. After that, 0.91 g (4.17 mmol) of (1R,2R,3S,5R)-2-amino-6,6-dimethylbicyclo[3.1.1]heptan-3-carboxylic acid hydrochloride (6), prepared according to Example 5, was added to the solution in one portion and the mixture was stirred for 30 min at 0° C., 3 h at room temperature, than for 30 min on boiling. The solution was evaporated to dryness and the resulting yellow crude product was recrystallized from isopropyl ether/ethyl acetate mixture. The isolated product 14 was: 0.78 g (80%).

Example 7

Ethyl (1R,2R,3S,5R)-2-amino-6,6-Dimethylbicyclo [3.1.1]Heptan-3-Carboxylate Hydrochloride (Compound 15) (Scheme 3)

Compound 15 was prepared by two methods:
Method 7a
1.16 g (7.0 mmol) of (1R,2R,5S,7R)-8,8-dimethyl-3-azatricyclo[5.1.1.0$^{2,5}$]nonan-4-one (10), prepared according to Example 1, was stirred in solution of 10% hydrochloric acid in dry ethanol (20 ml) at room temperature. After 1.5 h stirring, the solution was evaporated to dryness and the crystalline product obtained was recrystallized from isopropyl ether/ethyl acetate mixture.

Isolated compound: 1.54 g (89%); mp: 138-139° C.; $[\alpha]_D^{20}$=+23.0 (c=0.5, MeOH); IR=2918, 1729, 1373, 1189 cm$^{-1}$. Anal. Calcd. for $C_{12}H_{22}ClNO_2$ (247.76): C, 58.17; H, 8.95; N, 5.65. Found: C, 58.43; H, 9.26; N, 5.51. $^1$H NMR (CDCl$_3$) δ (ppm): 0.97 (3H, s, Me-6), 1.36 (3H, s, Me-6), 1.35 (3H, t, CH$_2$-CH$_3$, J=7.3 Hz), 1.56 (1H, d, H-4, J=11.1 Hz), 2.08-2.23 (3H, m,), 2.35-2.46 (2H, m), 3.51 (1H, dt, J=10.1, 3.0 Hz), 4.08 (1H, d, J=9.6 Hz), 4.24-4.35 (2H, m, CH$_2$-CH$_3$). $^{13}$C NMR (CDCl$_3$) δ (ppm): 13.7 (Me), 19.7 (Me), 24.4 (CH$_2$), 25.8 (CH), 29.4 (CH$_2$), 34.7 (CH) 39.4 (C$_q$), 39.6 (Me), 44.2 (CH), 50.4 (CH), 63.0 (CH$_2$), 176.7 (C=O).

Method 7b
0.22 ml (3.05 mmol) of thionyl chloride was added dropwise with stirring to 4 ml of dry methanol keeping the internal temperature below −12° C. during the addition. After that, 0.61 g (2.78 mmol) of (1R,2R,3S,5R)-2-amino-6,6-dimethylbicyclo[3.1.1]heptan-3-carboxylic acid hydrochloride 6, prepared according to Example 5, was added to the solution in one portion and the mixture was stirred for 30 min at 0° C. After standing for 3 h at room temperature the solution was boiled for 30 min. The solution was evaporated to dryness and the resulted yellow crude product was recrystallized from isopropyl ether/ethyl acetate mixture. The isolated product 15 was: 0.56 g (81%).

Example 8

Ethyl (1S,2S,3R,5S)-2-Amino-6,6-Dimethylbicyclo[3.1.1]Heptan-3-Carboxylate Hydrochloride (Compound 34) (Scheme 7)

The synthesis of 1S,2S,3R,5S enantiomer 33 was accomplished by analogy with Example 7a, starting from 1S,2S,5R,7S enantiomer azetidinone 33; $[\alpha]_D^{20}$=−19.6 (c=0.5, MeOH); all the spectroscopic data and mp were similar to those for 1R,2R,3S,5R enantiomer 15.

Example 9

(1R,2R,3S,5R)-(2-tert-Butoxycarbonylamino)-6,6-Dimethylbicyclo[3.1.1]Heptan-3-Carboxylic Acid (Compound 16) (Scheme 4)

0.66 g (3 mmol) of (1R,2R,3S,5R)-2-amino-6,6-dimethylbicyclo[3.1.1]heptan-3-carboxylic acid hydrochloride 6, prepared according to Example 5, was dissolved in 5 ml of distilled water at 0° C. and the pH of the solution was adjusted to pH=8 with 3% sodium hydroxide solution in the presence of bromothymol blue indicator (the amfoter form of amino acid is precipitated off). 5 ml of dioxane and 0.72 g (3.3 mmol) of Boc$_2$O was than added to the mixture. The reaction mixture was stirred at room temperature maintaining the pH=8 with 3% sodium hydroxide solution. After 6 h stirring at room temperature, the solution was cooled to 0° C. and acidified with 5% hydrochloric acid solution to pH=5, then the solution was extracted with chloroform (3×50 ml). The combined organic layer was dried (Na$_2$SO$_4$) and evaporated, and the white crystalline product obtained was recrystallized from n-hexane. The NMR measurement of the resulted product showed the present of approx. 12% isomer impurity (probably the trans compound) despite of the recrystallization process was repeated several times.

Isolated compound: 0.52 g (61%); mp: 151-153° C.; $[\alpha]_D^{20}$=+46.0 (c=0.5, MeOH); IR=3255, 2914, 1711, 1654, 1407, 1171 cm$^{-1}$. Anal. Calcd. for C$_{15}$H$_{25}$NO$_4$ (283.36): C, 63.58; H, 8.89; N, 4.94; Found: C, 63.79; H, 8.41; N, 5.19. $^1$H NMR (CDCl$_3$) δ (ppm): 0.88 (3H, s, Me-6), 1.24 (3H, s, Me-6), 1.47 (9H, s, CMe$_3$), 1.75 (1H, d, H-4, J=10.6 Hz), 1.84-1.99 (3H, m), 2.20-2.31 (2H, m), 3.21 (1H, dt, J=2.5, 10.1 Hz), 4.31 (1H, t, J=10.1 Hz), 7.33 (1H, d, J=10.1 Hz), 11.30 (1H, br s). $^{13}$C NMR (CDCl$_3$) δ (ppm): 20.6 (Me), 24.5 (CH$_2$), 26.5 (Me), 27.5 (CH$_2$), 28.6 (CMe$_3$), 39.0 (CH), 39.3 (C$_q$), 39.6 (CH), 46.7 (CH), 50.5 (CH), 81.4 (CMe$_3$), 155.8 (NC=O), 179.8 (C=O).

Example 10

(1S,2S,3R,5S)-(2-tert-Butoxycarbonylamino)-6,6-Dimethylbicyclo[3.1.1]Heptan-3-Carboxylic Acid (Compound 37) (Scheme 7)

The synthesis of 1S,2S,3R,5S enantiomer 37 was accomplished by analogy with Example 9, starting from 1S,2S,3R,5S enantiomer amino acid hydrochloride 7; $[\alpha]_D^{20}$=−44.1 (c=0.5, MeOH); all the spectroscopic data and mp were similar to those for (1R,2R,3S,5R) enantiomer 16.

The synthesis of 1S,2S,3R,5S-2-amino-6,6-dimethylbicyclo[3.1.1]heptan-3-carboxylic acid hydrochloride 7 was accomplished by analogy with Example 5, starting from 1S,2S,5R,7S enantiomer azetidinone 33; $[\alpha]_D^{20}$=−21.6 (c=0.5, MeOH); all the spectroscopic data and mp were similar to those for 1R,2R,3S,5R enantiomer 6.

Example 11

Ethyl (2S,1'R,2'R,3'S,5'R)-2-[(2'-tert-Butoxycarbonylamino)-6',6'-Dimethylbicyclo[3.1.1]Heptan-3'-Carbonyl]Amino-3-Phenylpropionate (Compound 17) (Scheme 4)

0.05 g of triethylamine and 0.065 g of isobutyl chloroformate were added to the solution of 0.14 g (0.49 mmol) of (1R,2R,3S,5R) Boc protected amino acid 16, prepared according to Example 9, in 5 ml of dry THF at −10° C. with vigorous stirring. After 10 min stirring and cooling, 2 ml dry THF solution of 0.095 g (0.49 mmol) of phenylalanine ethyl ester was added dropwise to the mixture at −10° C. The mixture was stirred at room temperature for further 5 h, than evaporated to dryness. The resulting oily crude product was dissolved in chloroform (30 ml) and the organic solution was washed first with ice-cold 5% solution of sodium hydrogen carbonate (20 ml), than with ice-cold 5% hydrochloric acid solution (20 ml). The organic layer was dried (Na$_2$SO$_4$) and evaporated. The obtained oily product was purified by flash chromatography on a silica gel column (n-hexane:ethyl acetate=6:1, Rf=0.35).

Isolated compound: 0.15 g (67%), viscous oil; $[\alpha]_D^{20}$=+22.5 (c=0.5, MeOH); IR=3411, 2978, 1711, 1497, 1366, 1161, 701 cm$^{-1}$. Anal. Calcd. for C$_{26}$H$_{38}$N$_2$O$_5$ (458.59): C, 68.10; H, 8.35; N, 6.11. Found: C, 67.76; H, 8.53; N, 6.38. $^1$H NMR (CDCl$_3$) δ (ppm): 0.88 (3H, s, Me), 1.22 (6H, s overlapped with t), 1.36 (9H, s, CMe$_3$), 1.62-2.20 (7H, m), 3.01 (1H, dt, J=3.5, 10.1 Hz), 3.15 (2H, ddd, J=3.5, 10.1, 42.3 Hz), 4.14 (2H, q, J=7.1, 14.1 Hz), 4.35 (1H, t, J=10.0 Hz), 4.74 (1H, q, J=6.1, 12.1 Hz), 5.28 (1H, d, J=10.1 Hz), 6.19 (1H, d, J=6.5 Hz), 7.9 (2H, d, J=7.1 Hz), 7.20-7.30 (3H, m). $^{13}$C NMR (CDCl$_3$) δ (ppm): 14.7 (Me), 20.9 (Me), 25.4 (CH$_2$), 26.8 (Me), 29.0 (CMe$_3$), 29.8 (CH$_2$), 38.6 (CH$_2$), 39.8 (C$_q$), 40.0 (Me), 40.5 (CH), 46.9 (CH), 49.5 (CH), 54.5 (CH), 62.1 (CH$_2$), 79.6 (CMe$_3$), 127.7 (CH$_{ar}$), 129.1 (CH$_{ar}$), 130.1 (CH$_{ar}$), 136.7 (C$_q$), 156.1 (C=O, Boc), 171.6 (C=O), 175.4 (C=O).

Example 12

Ethyl (2S,1'S,2'S,3'R,5'S)-2-[(2'-tert-Butoxycarbonylamino)-6',6'-Dimethylbicyclo[3.1.1]Heptan-3'-Carbonyl]Amino-3-Phenylpropionate (Compound 38) (Scheme 7)

The synthesis of 1S,2S,3R,5S enantiomer 38 was accomplished by analogy with Example 11, starting from 0.14 g (0.49 mmol) 1S,2S,3R,5S enantiomer 37 prepared according to Example 10.

Isolated compound: 0.12 g (54%); oil; $[\alpha]_D^{20}$=−10.0 (c=0.25, MeOH); IR=3306, 2923, 2852, 1744, 1681, 1500, 1330, 1160, 1042 cm$^{-1}$. Anal. Calcd. for C$_{26}$H$_{38}$N$_2$O$_5$ (458.59): C, 68.10; H, 8.35; N, 6.11. Found: C, 68.45; H, 8.01; N, 6.43. $^1$H NMR (CDCl$_3$) δ (ppm): 0.90 (3H, s, Me-6), 1.15 (3H, t, CH$_2$-CH$_3$, J=7.1 Hz), 1.23 (3H, s, Me-6), 1.38 (9H, s), 1.74 (1H, d, J=10.1 Hz), 1.87-2.21 (5H, m), 2.93 (1H, dd, J=14.1, 7.1 Hz), 3.03 (1H, dt, J=10.1, 4.0 Hz), 3.21 (1H, dd, J=14.1, 5.0 Hz), 4.09 (2H, dd, J=14.1, 7.1 Hz), 7.10-7.31 (5H, m). $^{13}$C NMR (CDCl$_3$) δ (ppm): 14.7, 20.9, 25.5, 26.9, 29.2, 29.8, 30.4, 39.3, 40.0, 40.4, 47.2, 49.6, 54.2, 62.0, 79.9, 127.8, 129.3, 130.0, 136.4, 156.1, 172.0, 175.3.

Example 13

(1R,2R,3S,5R)-2-(9H-Fluoren-9-yl-Methoxycarbonylamino)-6,6-Dimethylbicyclo[3.1.1]Heptan-3-Carboxylic Acid (Compound 18) (Scheme 4)

0.34 g (1.56 mmol) of (1R,2R,3S,5R)-2-amino-6,6-dimethylbicyclo[3.1.1]heptan-3-carboxylic acid hydrochloride (6), prepared according to Example 5, was dissolved in 6 ml of distilled water at 0° C. 0.50 g (6 mmol) of sodium hydrogen carbonate, 5 ml of acetonitrile and 0.51 g (1.5 mmol) of Fmoc-Osu was given to the solution at 0° C. After 12 h stirring at room temperature, the pH of the solution was adjusted to pH=2 with 10% hydrochloric acid solution and after 1 h stirring, the reaction mixture was extracted with ethyl acetate (3×20 ml). The combined organic layer was dried ($Na_2SO_4$), evaporated, and the crude product obtained was purified by flash chromatography on a silica gel column (n-hexane:ethyl acetate=9:1, Rf=0.35) resulting in white crystalline product.

Isolated compound: 0.40 g (63%); mp: 160-162° C.; $[\alpha]_D^{20}$=+2.0 (c=0.25, MeOH); IR=3260, 2908, 1711, 1652, 1414, 1332, 1201, 741 $cm^{-1}$. Anal. Calcd. for $C_{25}H_{27}NO_4$ (405.49): C, 74.05; H, 6.71; N, 3.45. Found: C, 74.19; H, 6.45; N, 3.53. $^1H$ NMR ($CDCl_3$) δ (ppm): 0.84 (3H, s), 1.23 (3H, s), 1.71 (1H, d, J=10.4 Hz), 1.81-2.25 (5H, m,), 3.08 (1H, t, J=9.1 Hz), 4.00-4.47 (4H, m), 7.24-7.75 (8H, m). $^{13}C$ NMR ($CDCl_3$) δ (ppm): 20.8, 24.8, 26.8, 28.8, 39.1, 39.6, 39.9, 46.9, 47.9, 50.8, 68.2, 120.6, 125.6, 125.9, 127.7, 128.3, 142.0, 142.1, 144.5, 144.8 158.7, 180.2.

Example 14

(1S,2S,3R,5S)-2-(9H-Fluoren-9-yl-Methoxycarbonylamino)-6,6-Dimethylbicyclo[3.1.1]Heptan-3-Carboxylic Acid (Compound 36) (Scheme 7)

The synthesis of 1S,2S,3R,5S enantiomer 36 was accomplished by analogy with Example 13, starting from 1S,2S,3R,5S enantiomer amino acid hydrochloride (7) (prepared according to Example 10); $[\alpha]_D^{20}$=−2.0 (c=0.25, MeOH); all the spectroscopic data and mp were similar to those for 1R,2R,3S,5R enantiomer 18.

Example 15

(1S,2S,3R,5S)-2-Dimethylamino-6,6-Dimethylbicyclo[3.1.1]Heptan-3-Carboxylic Acid Hydrochloride (Compound 19) (Scheme 4)

0.50 g (2.27 mmol) of amino acid hydrochloride 6 prepared according to Example 5, was dissolved in 15 ml of distilled water, followed by addition of 0.43 g (5.0 mmol) of 35% formaldehyde solution and 0.20 g of 10% Pd/C catalyst. The mixture was stirred at room temperature and 10 bar under $H_2$ atmosphere for 12 h. The mixture was than filtered and evaporated to dryness. The resulting crystalline product was rubbed with acetone, than filtered off.

Isolated compound: 0.50 g (89%); mp: 144-145° C.; $[\alpha]_D^{20}$=+10.7 (c=0.505, MeOH); IR=2952, 1709, 1458, 1186 $cm^{-1}$. Anal. Calcd. for $C_{12}H_{22}ClNO_2$ (247.76): C, 58.17; H, 8.95; N, 5.65. Found: C, 58.23; H, 8.69; N, 5.37. $^1H$ NMR ($CDCl_3$) δ (ppm): 0.89 (3H, s, Me-6), 1.35 (3H, s, Me-6), 1.62 (1H, d, H-4, J=11.1 Hz), 2.03-2.10 (1H, m,), 2.21-2.56 (4H, m), 2.88 (3H, s), 2.92 (3H, s), 3.51 (1H, t, J=9.3 Hz), 3.76 (1H, d, J=8.6 Hz). $^{13}C$ NMR ($CDCl_3$) δ (ppm): 19.4 (Me), 23.4 ($CH_2$), 25.9 (Me), 29.5 ($CH_2$), 34.3 (CH), 39.3 (CH), 40.3 (CH), 40.4 ($C_q$), 42.3 (Me), 44.1 (Me), 67.2 (CH), 179.9 (C=O).

Example 16

Ethyl (1R,2R,3S,5R)-2-Benzylamino-6,6-Dimethylbicyclo[3.1.1]Heptan-3-Carboxylate Hydrochloride (Compound 20) (Scheme 5)

1.05 g (5 mmol) of ethyl (1R,2R,3S,5R)-2-amino-6,6-dimethylbicyclo[3.1.1]heptan-3-carboxylate (15) base, prepared according to Example 7a, and 0.53 g (5 mmol) of benzaldehyde was dissolved in 30 ml of dry ethanol. The solution was stirred at room temperature for 2 h, than evaporated to dryness. The resulting viscous oil was dissolved in 30 ml of dry ethanol, followed by addition of 0.57 g (0.015 mmol) of sodium borohydride in small portions at 0° C. After 6 h stirring at room temperature, the solution was evaporated to dryness, the residual was dissolved in 50 ml of ice-cold water and extracted with chloroform (3×50 ml). The combined organic layer was dried ($Na_2SO_4$) and evaporated, and the hydrochloride salt 20, prepared from the amino ester base with 10% solution of hydrochloric acid in dry ethanol, was recrystallized from isopropyl ether.

Isolated compound: 1.18 g (70%); mp: 165-168° C.; $[\alpha]_D^{20}$=+16.4 (c=0.525, MeOH); IR=2919, 1733, 1445, 1183, 705 $cm^{-1}$. Anal. Calcd. for $C_{19}H_{28}ClNO_2$ (337.88): C, 67.54; H, 8.35; N, 4.15. Found: C, 67.79; H, 8.21; N, 4.47. $^1H$ NMR ($CDCl_3$) δ (ppm): 0.91 (3H, s, Me-6), 1.34 (3H, t, $CH_2$-$CH_3$, J=7.1 Hz), 1.37 (3H, s, Me-6), 1.63 (1H, d, H-4, J=10.1 Hz), 2.07-2.11 (1H, m,), 2.16-2.23 (1H, m), 2.36-2.51 (3H, m), 3.46 (1H, dt, J=10.1, 2.5 Hz), 3.97 (1H, d, J=9.1 Hz), 4.19-4.37 (4H, m, $CH_2$-$CH_3$ and $CH_2$Ph), 7.52-7.58 (5H, m, Ph). $^{13}C$ NMR ($CDCl_3$) δ (ppm): 13.6 (Me), 19.4 (Me), 24.0 ($CH_2$), 25.8 (CH), 29.5 ($CH_2$), 33.9 (CH), 39.7 (Me), 40.1 ($C_q$), 42.4 (CH), 50.4 ($CH_2$), 57.4 (CH), 63.2 ($CH_2$), 129.8 (CH), 130.2 (CH), 130.3 (CH), 131.0 ($C_q$), 177.6 (C=O).

Example 17

(1S,2S,3R,5S)-2-Benzylamino-6,6-Dimethylbicyclo[3.1.1]Heptan-3-Carboxylic Acid Hydrochloride (Compound 21) (Scheme 5)

0.80 g (2.37 mmol) of compound 20, prepared according to Example 16, was dissolved in 40 ml of 10% solution of hydrochloric acid. The mixture was stirred at room temperature while the hydrolysis was accomplished (the progress of the reaction was monitored by means of $^1H$ NMR). When the hydrolysis was accomplished, the solution was evaporated to dryness and the resulting crystalline product was rubbed with acetone, than filtered off.

Isolated compound: 0.46 g (63%); mp: 171-172° C.; $[\alpha]_D^{20}$=+12.9 (c=0.52, MeOH); IR=2918, 1697, 1456, 1200, 697 $cm^{-1}$. Anal. Calcd. for $C_{17}H_{24}ClNO_2$ (309.83): C, 65.90; H, 7.81; N, 4.52. Found: C, 65.83; H, 8.12; N, 4.77. $^1H$ NMR ($CDCl_3$) δ (ppm): 0.89 (3H, s, Me-6), 1.35 (3H, s, Me-6), 1.64 (1H, d, H-4, J=11.1 Hz), 2.06-2.12 (1H, m,), 2.18-2.25 (1H, m), 2.32-2.53 (3H, m), 3.35-3.42 (1H, m), 3.93 (1H, d, J=9.1 Hz), 4.27 (2H, dd, J=39.3, 13.6 Hz, $CH_2$Ph), 7.48-7.57 (5H, m, Ph). $^{13}C$ NMR ($CDCl_3$) δ (ppm): 19.4 (Me), 23.9 ($CH_2$), 25.7 (Me), 29.7 ($CH_2$), 33.6 (CH), 39.7 (CH), 40.1 ($C_q$), 42.6 (CH), 50.3 ($CH_2$), 57.2 (CH), 129.7 (CH), 130.2 (CH), 130.3 (CH), 130.9 ($C_q$), 179.7 (C=O).

Example 18

(1R,2R,3S,5R)-(2-Amino-6,6-Dimethylbicyclo[3.1.1]Hept-3-yl)-Methanol Hydrochloride (Compound 22) (Scheme 5)

To a slurry of LiAlH$_4$ 0.93 g (24.5 mmol) in 150 ml of dry THF, 2.00 g (9.5 mmol) of (1R,2R,3S,5R) amino ester liberated from compound 15 (prepared according to Example 7a) was added dropwise at 0° C. After stirring at room temperature for 1.5 h (the reduction was monitored by means of TLC), the mixture was decomposed with the mixture of 10 ml of THF and 2.0 ml of water under ice cooling. The inorganic material was filtered off and washed with THF. After drying (Na$_2$SO$_4$) and evaporation, pale-yellow oil was obtained. The amino alcohol obtained was purified as the hydrochloride with recrystallizing from diethyl ether/ethanol mixture.

Isolated compound: 1.45 g (70%): mp: 179-183° C.; [α]$_D^{20}$=−16.4 (c=0.5, MeOH); IR=3123, 2917, 1529, 1457, 1051 cm$^{-1}$. Anal. Calcd. for C$_{10}$H$_{20}$ClNO (205.72): C, 58.38; H, 9.80; N, 6.81. Found: C, 58.61; H, 10.11; N, 6.49. $^1$H NMR (CDCl$_3$) δ (ppm): 0.95 (3H, s, Me-6), 1.15 (1H, d, H-4, J=11.1 Hz), 1.28 (3H, s, Me-6), 1.44 (1H, dt, J=4.0, 14.1 Hz, H-7), 1.97-2.03 (1H, m, H-5), 2.09-2.18 (2H, m, H-1, H-7), 2.27-2.34 (1H, m, H-4), 2.59-2.70 (1H, m, H-3), 3.73 (2H, ddd, J=5.0, 11.58, 40.2 Hz, CH$_2$-OH), 3.98 (1H, d, J=9.6 Hz, H-2). $^{13}$C NMR (CDCl$_3$) δ (ppm): 19.9 (Me), 25.2 (CH$_2$), 25.8 (Me), 29.0 (CH$_2$), 30.3 (CH), 38.6 (C$_q$), 40.0 (CH), 45.0 (CH), 52.9 (CH), 65.0 (CH$_2$).

Example 19

(1S,2S,3R,5S)-(2-Amino-6,6-Dimethylbicyclo[3.1.1]Hept-3-yl)-Methanol Hydrochloride (Compound 35) (Scheme 7)

The synthesis of 1S,2S,3R,5S enantiomer 35 was accomplished by analogy with Example 18, starting from 1S,2S,3R,5S enantiomer amino ester 34 which was prepared according to Example 8; [α]$_D^{20}$=+13.4 (c=0.5, MeOH); all the spectroscopic data and mp were similar to those for 1R,2R,3S,5R enantiomer 22.

Example 20

(1R,2R,3S,5R)-(6,6-Dimethyl-2-Methylaminobicyclo[3.1.1]Heptan-3-yl)-Methanol Hydrochloride (Compound 23) (Scheme 5)

To a slurry of LiAlH$_4$ 2.82 g (74.32 mmol) in 150 ml of dry THF, 10 ml THF solution of 4.78 g (16.9 mmol) of N-Boc amino acid 16 (prepared according to Example 9) was added dropwise at room temperature. After stirring at room temperature for 6 h (the reduction was monitored by means of TLC), the mixture was decomposed with the mixture of 30 ml of THF and 6.0 ml of water under ice cooling. After one hour of standing the inorganic material was filtered off and washed with THF. After drying (Na$_2$SO$_4$) and evaporation, a pale-yellow oil was obtained. The amino alcohol was purified as the hydrochloride with recrystallizing from diethyl ether/ethanol mixture.

Isolated compound: 1.44 g (39%): mp: 192-193° C.; [α]$_D^{20}$=−15.7 (c=0.5, MeOH); IR=3308, 3123, 2916, 2475, 1595, 1458, 1049 cm$^{-1}$. Anal. Calcd. for C$_{11}$H$_{22}$ClNO (219.14): C, 60.12; H, 10.09; N, 7.20. Found: C, 60.33; H, 10.27; N, 6.95. $^1$H NMR (D$_2$O) δ (ppm): 0.99 (3H, s), 1.18 (1H, d, J=10.6 Hz), 1.35 (3H, s), 1.48-1.55 (1H, m), 2.03-2.10 (1H, m), 2.15-2.24 (1H, m), 2.33-2.47 (2H, m), 2.74 (3H, s), 2.72-280 (1H, m), 3.73-3.91 (3H, m). $^{13}$C NMR (CDCl$_3$) δ (ppm): 20.0 (Me), 25.1 (CH$_2$), 26.1 (Me), 29.2 (CH$_2$), 31.1 (CH), 32.1 (CH), 38.4 (C), 39.9 (CH), 41.1 (CH), 62.0 (Me), 65.1 (CH$_2$).

Example 21

(1R,2R,3S,5R)-(2-Benzylamino-6,6-Dimethylbicyclo[3.1.1]Heptan-3-yl)-Methanol Hydrochloride (Compound 24) (Scheme 5)

To a slurry of LiAlH$_4$ 0.78 g (20.4 mmol) in 50 ml of dry THF, 25 ml THF solution of 3.06 g (10.2 mmol) of 1R,2R,3S,5R amino ester 20 (prepared according to Example 16) was added dropwise at room temperature. After stirring at room temperature for 4 h (the reduction was monitored by means of TLC), the mixture was decomposed with the mixture of 20 ml of THF and 2.0 ml of water under ice cooling. The inorganic material was filtered off and washed with THF. After drying (Na$_2$SO$_4$) and evaporation, a pale-yellow oil was obtained. The prepared amino alcohol was purified as the hydrochloride with recrystallizing from diethyl ether/ethanol mixture.

Isolated compound: 1.82 g (61%): mp: 252-253° C.; [α]$_D^{20}$=−8.5 (c=0.5, MeOH); IR=3177, 2927, 2741, 1597, 1457, 1048 cm$^{-1}$. Anal. Calcd. for C$_{17}$H$_{26}$ClNO (295.85): C, 69.02; H, 8.86; N, 4.73. Found: 68.85; H, 8.67; N, 4.97. $^1$H NMR (D$_2$O) δ (ppm) 0.94 (3H, s, Me-6), 1.23 (1H, d, H-4, J=11.1 Hz), 1.36 (3H, s, Me-6), 1.44 (1H, dt, J=4.0, 14.1 Hz, H-7), 2.02-2.23 (2H, m), 2.37-2.55 (3H, m), 2.64-2.75 (1H, m), 3.74-3.94 (3H, m), 4.23 (1H, d, J=13.1), 4.44 (1H, d, J=13.1 Hz). $^{13}$C NMR (CDCl$_3$) δ (ppm): 19.8 (Me), 25.3 (CH$_2$), 25.9 (Me), 28.8 (CH$_2$), 30.7 (CH), 38.5 (C$_q$), 39.7 (CH), 41.9 (CH), 49.9 (CH$_2$), 59.8 (CH), 65.6 (CH$_2$), 129.8 (4×CH), 130.1 (CH), 131.5 (C$_q$).

Example 22

(1R,2R,3S,5R)-(2-Dimethylamino-6,6-Dimethylbicyclo[3.1.1]Hept-3il)-Methanol Hydrochloride (Compound 25) (Scheme 5)

3.50 g (20.7 mmol) of the base of amino alcohol hydrochloride 22, prepared according to Example 18, was dissolved in a mixture of 40 ml of formic acid and 40 ml of 35% formaldehyde solution. The mixture was refluxed for 1 h and, after cooling down, the solution was made alkaline with 20% aqueous KOH and extracted with chloroform (3×100 ml). The combined organic phase was dried (Na$_2$SO$_4$) and evaporated to give 2.50 g of an almost colourless oil which was used in the next step without further purification. To a slurry of 1.94 g (51.2 mmol) of LiAlH$_4$ in 100 ml of dry THF, the oily product obtained above in 10 ml of dry THF was added dropwise at room temperature After stirring and refluxing for 3 h (the reduction was monitored by means of TLC), the mixture was decomposed with the mixture of 20 ml of THF and 4.0 ml of water under ice cooling. After stirring for 1 h, the inorganic material was filtered off and washed with THF (2×100 ml). After drying (Na$_2$SO$_4$) and evaporation, a pale-yellow oil was obtained. The amino alcohol 25 was purified as the hydrochloride recrystallizing from diethyl ether/ethanol mixture.

Isolated compound: 2.45 g (51%): mp: 176-177° C.; [α]$_D^{20}$=+0.9 (c=0.5, MeOH); IR=3332, 2924, 2711, 1484, 1042 cm$^{-1}$. Anal. Calcd. for C$_{12}$H$_{24}$ClNO (233.78): C, 61.65; H, 10.35; N, 5.99. Found: C, 61.84; H, 10.12; N, 6.19. $^1$H NMR (CDCl$_3$) δ (ppm): 0.83 (3H, s, Me-6), 1.27 (3H, s, Me-6), 1.46 (1H, d, H-4, J=10.6 Hz), 1.57-1.64 (2H, m), 1.83-1.99 (2H, m), 2.19-2.27 (1H, m), 2.34 (1H, t, J=5.0 Hz), 2.71 (3H, br s), 2.82 (3H, br s), 3.67-3.75 (2H, m), 3.79-3.86 (1H, m), 5.83 (1H, br s), 9.68 (1H, br s). $^{13}$C NMR (CDCl$_3$) δ (ppm): 19.9 (2×Me), 25.0 (CH$_2$), 26.0 (CH), 27.0 (CH$_2$), 31.4 (2×Me), 38.7 (CH), 39.1 (CH), 39.8 (C$_q$), 64.1 (CH$_2$), 66.9 (CH).

Example 23

Ethyl (1R,2R,3R,5R)-2-Amino-6,6-Dimethylbicyclo[3.1.1]Heptan-3-Carboxylate Hydrochloride (Compound 26) (Scheme 6)

To a solution of 0.23 g (10 mmol) of sodium in 30 ml of dry ethanol, 1.05 g (5 mmol) base of ethyl (1R,2R,3S,5R)-2-amino-6,6-dimethylbicyclo[3.1.1]heptan-3-carboxylate (15), prepared according to Example 7, was added in one portion. The solution was stirred at room temperature until isomerisation was accomplished (approx. 4 h, the isomerisation process was monitored by means of TLC and GC). The solution was evaporated to approx. 5 ml, diluted with ice-cold water (50 ml) and extracted with ethyl acetate (3×50 ml). The combined organic layer was dried (Na$_2$SO$_4$) and evaporated, and the hydrochloride salt 26, prepared from the resulted amino ester base with 15% solution of hydrochloric acid in dry ethanol, was recrystallized from isopropyl ether.

Isolated compound: 0.85 g (69%); mp: 147-148° C.; [α]$_D^{20}$=−32.4 (c=0.5, MeOH); IR=2926, 1734, 1509, 1292, 1193 cm$^{-1}$. Anal. Calcd. for C$_{12}$H$_{22}$ClNO$_2$ (247.76): C, 58.17; H, 8.95; N, 5.65. Found: C, 58.35; H, 8.78; N, 5.79. $^1$H NMR (CDCl$_3$) δ (ppm): 0.88 (3H, s, Me-6), 1.34 (3H, s, Me-6), 1.36 (3H, t, CH$_2$-CH$_3$, J=7.1 Hz), 1.56 (1H, d, H-4, J=11.1 Hz), 2.05 (1H, dd, J=13.6, 9.1 Hz), 2.10-2.23 (2H, m), 2.35-2.46 (2H, m), 3.05 (1H, dd, J=9.1, 18.1 Hz), 4.10 (1H, d, J=89.6 Hz), 4.33 (2H, dd, J=7.1, 14.1 Hz, CH$_2$-CH$_3$). $^{13}$C NMR (CDCl$_3$) δ (ppm): 13.8 (Me), 19.1 (Me), 23.0 (CH$_2$), 25.8 (CH), 27.5 (CH$_2$), 38.4 (CH), 39.3 (Me), 39.7 (C$_q$), 43.4 (CH), 52.3 (CH), 63.0 (CH$_2$), 175.9 (C=O).

Example 24

Ethyl (1S,2S,3S,5S)-2-Amino-6,6-Dimethylbicyclo[3.1.1]Heptan-3-Carboxylate Hydrochloride (Compound 39) (Scheme 8)

The synthesis of 1S,2S,3S,5S enantiomer 39 was accomplished by analogy with Example 23, starting from 1S,2S,3R,5S enantiomer amino ester 34 which was prepared according to Example 8; [α]$_D^{20}$=+31.0 (c=0.5, MeOH); all the spectroscopic data and mp were similar to those for 1R,2R,3R,5R enantiomer 26.

Example 25

Ethyl (1R,2R,3R,5R)-2-Benzylamino-6,6-Dimethylbicyclo[3.1.1]Heptan-3-Carboxylate Hydrochloride (Compound 27) (Scheme 6)

1.05 g (5 mmol) of ethyl (1R,2R,3R,5R)-2-amino-6,6-dimethylbicyclo[3.1.1]heptan-3-carboxylate (26) base prepared according to Example 23, and 0.53 g (5 mmol) of benzaldehyde was dissolved in 30 ml of dry ethanol. The solution was stirred at room temperature for 2 h, than evaporated to dryness. The resulting viscous oil was dissolved in 30 ml of dry ethanol, followed by addition of 0.57 g (0.015 mmol) of sodium borohydride in small portions at 0° C. After 6 h stirring at room temperature, the solution was evaporated to dryness, the resulting mass was dissolved in 50 ml of ice-cold water and extracted with chloroform (3×50 ml). The combined organic layer was dried (Na$_2$SO$_4$) and evaporated, and the hydrochloride 27, prepared from the amino ester base with 10% solution of hydrochloric acid in dry ethanol, was recrystallized from isopropyl ether.

Isolated compound: 1.23 g (73%); mp: 134-136° C.; [α]$_D^{20}$=−3 (c=0.25, MeOH); IR=2948, 2778, 1731, 1577, 1182, 747 cm$^{-1}$. Anal. Calcd. for C$_{19}$H$_{28}$ClNO$_2$ (337.88): C, 67.54; H, 8.35; N, 4.15. Found: C, 67.79; H, 8.21; N, 4.47. $^1$H NMR (CDCl$_3$) δ (ppm): 0.71 (3H, s), 1.22 (3H, t, J=7.1 Hz), 1.30 (3H, s), 1.53 (1H, d, J=10.6 Hz), 1.89 (1H, dd, J=13.6, 8.8 Hz), 2.02-2.09 (1H, m), 2.31-2.42 (3H, m), 3.08 (1H, dd, J=18.8, 8.8 Hz), 3.89 (1H, d, J=8.4 Hz), 4.10-4.22 (1H, m), 4.27 (2H, dd, J=42.7, 13.3 Hz), 7.45-7.56 (5H, m, Ph). $^{13}$C NMR (CDCl$_3$) δ (ppm): 13.8, 19.0, 23.4, 25.9, 28.0, 37.8, 39.4, 39.7, 40.5, 49.1, 57.6, 64.8, 129.8, 130.3, 130.6, 131.0, 175.5.

Example 26

(1R,2R,3R,5R)-2-Amino-6,6-Dimethylbicyclo[3.1.1]Heptan-3-Carboxylic Acid (Compound 29) (Scheme 6)

Method 26a 0.23 g (1.09 mmol) of base liberated from ethyl (1R,2R,3R,5R)-2-amino-6,6-dimethylbicyclo[3.1.1]heptan-3-carboxylate hydrochloride 26 (prepared according to Example 23) was dissolved in the mixture of 10 ml of dioxane and 10 ml of distilled water and the solution was heated at 80° C. with monitoring by means of TLC. When the reaction was accomplished (indicated by elimination of the starting ester), the mixture was evaporated to dryness and the resulting white crystalline product was rubbed with acetone, filtered off and recrystallized from acetone/water mixture.

Isolated compound: 0.13 g (65%); mp: 250-252° C.; [α]$_D^{20}$=−42.7 (c=0.5, MeOH); IR=2924, 1624, 1552, 1404 cm$^{-1}$. Anal. Calcd. for C$_{10}$H$_{17}$NO$_2$ (183.25): C, 65.54; H, 9.35; N, 7.64. Found: 65.21; H, 9.87; N, 7.19. $^1$H NMR (CDCl$_3$) δ (ppm): 0.82 (3H, s, Me-6), 1.26 (3H, s, Me-6), 1.49 (1H, d, J=10.8 Hz), 1.83-1.93 (1H, m), 1.98-2.11 (2H, m), 2.20-2.30 (2H, m), 2.61-2.70 (1H, m), 3.90 (1H, d, J=8.6 Hz). $^{13}$C NMR (CDCl$_3$) δ (ppm): 19.1 (Me), 22.8 (CH$_2$), 25.8 (Me), 28.1 (CH$_2$), 39.7 (CH), 39.9 (C$_q$), 40.6 (CH), 43.4 (CH), 53.6 (CH), 181.5 (C=O).

Method 26b 0.56 g (85%) of (1R,2R,3R,5R)-2-amino-6,6-dimethylbicyclo[3.1.1]heptan-3-carboxylic acid hydrochloride 8 was prepared according to Example 17, starting from 0.74 g (3.0 mmol) of ethyl (1R,2R,3R,5R)-2-amino-6,6-dimethylbicyclo[3.1.1]heptan-3-carboxylate hydrochloride (26) (prepared according to Example 23).

Compound 8: mp: 241-242° C.; [α]$_D^{20}$=−32.6 (c=0.5, MeOH); IR=2913, 1716, 1511, 1247 cm$^{-1}$. Anal. Calcd. for C$_{10}$H$_{18}$ClNO$_2$ (219.71): C, 54.67; H, 8.26; N, 6.38. Found: C, 54.79; H, 8.39; N, 6.21. $^1$H NMR (CDCl$_3$) δ (ppm): 0.88 (3H, s, Me-6), 1.34 (3H, s, Me-6), 1.56 (1H, d, J=11.1 Hz), 2.05 (1H, dd, J=13.8, 8.8 Hz), 2.13 (1H, dd, J=9.8, 4.8 Hz), 2.20 (1H, t, J=5.5 Hz), 2.35-2.45 (2H, m), 2.99-3.07 (1H, m), 4.08 (1H, d, J=8.6 Hz). $^{13}$C NMR (CDCl$_3$) δ (ppm): 19.1 (Me), 23.0 (CH$_2$), 25.8 (Me), 27.4 (CH$_2$), 38.2 (CH), 39.4 (CH), 39.8 (C$_q$), 43.4 (CH), 52.4 (CH), 177.7 (C=O).

0.56 g (2.58 mmol) of (1R,2R,3R,5R)-2-amino-6,6-dimethylbicyclo[3.1.1]heptan-3-carboxylic acid hydrochloride (8) was dissolved in 8 ml of distilled water and then pH of the solution was adjusted to pH=7.4 with 10% solution of NaHCO$_3$ with ice cooling in the presence of methylthymol-blue indicator. After 1 h stirring at 0° C. the precipitated crystalline product was filtered and washed with a small amount of ice-cold distilled water. Isolated compound: 0.30 g (65%);

Example 27

(1R,2R,3R,5R)-(2-tert-Butoxycarbonylamino)-6,6-Dimethylbicyclo[3.1.1]Heptan-3-Carboxylic Acid (Compound 31) (Scheme 6)

The synthesis of compound 31 was accomplished by analogy with Example 9, starting from 0.66 g (3 mmol) of (1R,2R,3R,5R)-2-amino-6,6-dimethylbicyclo[3.1.1]-heptan-3-carboxylic acid hydrochloride 8, which was prepared according to Example 26b.

Isolated compound: 0.55 g (65%); mp: 85-87° C.; $[\alpha]_D^{20}$=−43.3 (c=0.5, MeOH); IR=3336, 2923, 1711, 1659, 1366, 1176 cm$^{-1}$. Anal. Calcd. for C$_{15}$H$_{25}$NO$_4$ (283.36): C, 63.58; H, 8.89; N, 4.94. Found: C, 63.84; H, 8.99; N, 5.26. $^1H$NMR (CDCl$_3$) δ (ppm): 0.94 (3H, s), 1.23 (3H, s), 1.35 (1H, d, J=10.1 Hz), 1.43 (9H, s), 1.94-2.21 (5H, m), 2.53-2.64 (1H, m), 4.26-4.36 (1H, m), 4.73 (1H, br s). $^{13}$C NMR (CDCl$_3$) δ (ppm): 20.1, 24.1, 27.2, 28.4, 29.0, 40.2, 40.4, 42.7, 46.7, 52.1, 81.0, 155.7, 179.8.

Example 28

(1S,2S,3S,5S)-(2-tert-Butoxycarbonylamino)-6,6-Dimethylbicyclo[3.1.1]Heptan-3-Carboxylic Acid (Compound 42) (Scheme 8)

The synthesis of 1S,2S,3S,5S-2-amino-6,6-dimethylbicyclo[3.1.1]heptan-3-carboxylic acid enantiomer 9 was accomplished by analogy with Example 19, starting from 1S,2S,3S,5S enantiomer amino ester 39, prepared according to Example 24; $[\alpha]_D^{20}$=+30.1 (c=0.5, MeOH); all the spectroscopic data and mp were similar to those for 1R,2R,3R,5R enantiomer 8.

The synthesis of 1S,2S,3S,5S enantiomer 42 was accomplished by analogy with Example 9, starting from 0.66 g (3 mmol) of (1S,2S,3S,5S)-2-amino-6,6-dimethylbicyclo[3.1.1]heptan-3-carboxylic acid hydrochloride 9 prepared above, $[\alpha]_D^{20}$=+41.1 (c=0.5, MeOH); all the spectroscopic data and mp were similar to those for 1R,2R,3R,5R enantiomer 31.

Example 29

(1R,2R,3R,5R)-(2-Amino-6,6-Dimethylbicyclo[3.1.1]Hept-3-yl)-Methanol Hydrochloride (Compound 28) (Scheme 6)

To a slurry of LiAlH$_4$ 0.93 g (24.5 mmol) in 150 ml of dry THF, 2.00 g (9.5 mmol) of (1R,2R,3R,5R) amino ester liberated from compound 26 (prepared according to Example 23) was added dropwise at 0° C. After stirring at room temperature for 1.5 h (the reduction was monitored by means of TLC), the mixture was decomposed with the mixture of 10 ml of THF and 2.0 ml of water under ice cooling. After 1 h stirring at room temperature, the inorganic material was filtered off and washed with THF. After drying (Na$_2$SO$_4$) and evaporation, the amino alcohol obtained as a pale-yellow oil was purified as the hydrochloride with recrystallizing from diethyl ether/ethanol mixture.

Isolated compound: 1.62 g (78%); mp: 199-202° C.; $[\alpha]_D^{20}$=−7.9 (c=0.52, MeOH); IR=3298, 2905, 1512, 1040 cm$^{-1}$. Anal. Calcd. for C$_{10}$H$_{20}$ClNO (205.72): C, 58.38; H, 9.80; N, 6.81. Found: C, 58.49; H, 9.71; N, 6.93. $^1$H NMR (CDCl$_3$) δ (ppm): 0.86 (3H, s), 1.32 (3H, s), 1.50-1.59 (1H, m), 1.62 (1H, d, J=10.6 Hz), 2.03-2.20 (4H, m), 2.28-2.36 (1H, m), 3.63 (1H, d, J=8.1 Hz), 3.73 (2H, ddd, J=2.5, 5.5, 11.1 Hz). $^{13}$C NMR (CDCl$_3$) δ (ppm): 19.1 (Me), 23.1 (CH$_2$), 26.2 (Me), 26.3 (CH$_2$), 35.1 (CH), 89.7 (CH), 40.0 (C$_q$), 44.2 (CH), 54.6 (CH), 64.5 (CH$_2$).

Example 30

(1S,2S,3S,5S)-(2-Amino-6,6-Dimethylbicyclo[3.1.1]Hept-3-yl)-Methanol Hydrochloride (Compound 40) (Scheme 8)

The synthesis of 1S,2S,3S,5S enantiomer 40 was accomplished by analogy with Example 29, starting from 1S,2S,3S,5S enantiomer amino ester 31 which was prepared according to Example 27; $[\alpha]_D^{20}$=+8.1 (c=0.5, MeOH); all the spectroscopic data and mp were similar to those for 1R,2R,3R,5R enantiomer 28.

Example 31

(1R,2R,3R,5R)-2-(9H-Fluoren-9-yl-Methoxycarbonylamino)-6,6-Dimethylbicyclo[3.1.1]Heptan-3-Carboxylic Acid (Compound 30) (Scheme 6)

The synthesis of 1R,2R,3R,5R enantiomer 30 was accomplished by analogy with Example 13, starting from 1R,2R,3R,5R enantiomer amino acid hydrochloride 8 which was prepared according to Example 26b; mp: 155-157° C.; $[\alpha]_D^{20}$=−4 (c=0.25, MeOH); IR=3340, 2926, 1693, 1536, 1450, 1252, 739 cm$^{-1}$. Anal. Calcd. for C$_{25}$H$_{27}$NO$_4$ (405.49): C, 74.05; H, 6.71; N, 3.45. Found: C, 74.27; H, 6.52; N, 3.49. $^1$H NMR (CDCl$_3$) δ (ppm): 0.90 (3H, s), 1.20 (3H, s), 1.34 (1H, d, J=10.6 Hz), 1.81-2.14 (5H, m), 2.56-2.62 (1H, m), 4.17 (1H, t, J=6.5 Hz), 4.28-4.46 (3H, m), 4.97 (1H, br s), 7.20-7.80 (8H, m). $^{13}$C NMR (CDCl$_3$) δ (ppm): 20.1, 24.2, 27.2, 28.4, 32.1, 40.2, 42.6, 46.7, 47.9, 52.5, 67.5, 120.6, 125.8, 127.7, 128.3, 142.0, 144.6, 148.5, 179.8.

Example 32

(1S,2S,3S,5S)-2-(9H-Fluoren-9-yl-Methoxycarbonylamino)-6,6-Dimethylbicyclo[3.1.1]Heptan-3-Carboxylic Acid (Compound 41) (Scheme 8)

The synthesis of 1S,2S,3S,5S enantiomer 41 was accomplished by analogy with Example 13, starting from 1S,2S,3S,5S enantiomer amino acid hydrochloride 9 which was prepared according to Example 28; $[\alpha]_D^{20}$=+6 (c=0.25, MeOH); all the spectroscopic data and mp were similar to those for 1R,2R,3R,5R enantiomer 30.

Example 33

Ethyl (2S,1'R,2'R,3'R,5'R)-2-{[(2'-tert-Butoxycarbonylamino)-6',6'-Dimethylbicyclo[3.1.1]Heptan-3'-Carbonyl)]Amino}-3-Phenylpropionate (Compound 32) (Scheme 6)

The synthesis of 2S,1'R,2'R,3'R,5'R compound 32 was accomplished by analogy with Example 11, starting from 0.14 g (0.49 mmol) of 1R,2R,3R,5R enantiomer 31.

Isolated compound: 0.09 g (40%); mp: 185-188° C.; $[\alpha]_D^{20}=-15$ (c=0.25, MeOH); IR=3270, 2926, 1750, 1684, 1651, 1558, 1196 cm$^{-1}$. Anal. Calcd. for $C_{26}H_{38}N_2O_5$ (458.59): C, 68.10; H, 8.35; N, 6.11. Found: C, 68.51; H, 7.96; N, 6.47. $^1$H NMR (CDCl$_3$) δ (ppm): 0.79 (3H, s), 1.19 (3H, t, J=7.1 Hz), 1.20 (3H, s), 1.30 (1H, d, J=10.5 Hz), 1.46 (9H, s), 1.90-2.19 (5H, m), 2.33-2.47 (1H, m), 3.04-3.17 (2H, m), 4.12 (2H, dd, J=14.2, 7.1 Hz), 4.20-4.29 (1H, m), 4.25 (1H, t, J=8.6 Hz), 4.77-4.86 (1H, m), 7.17-7.32 (5H, m). $^{13}$C NMR (CDCl$_3$) δ (ppm): 14.8, 20.1, 24.2, 27.0, 28.2, 29.1, 30.4, 38.7, 40.3, 43.6, 47.3, 51.9, 54.5, 61.9, 80.7, 127.5, 129.1, 130.1, 137.4, 156.2, 172.6, 174,4.

Example 34

Ethyl (2S,1'S,2'S,3'S,5'S)-2-{[(2'-tert-Butoxycarbonylamino)-6',6'-Dimethylbicyclo[3.1.1]Heptan-3'-Carbonyl)]Amino}-3-Phenylpropionate (Compound 43) (Scheme 8)

The synthesis of 2S,1'S,2'S,3'S,5'S compound 43 was accomplished by analogy with Example 11, starting from 0.14 g (0.49 mmol) of 1S,2S,3S,5S enantiomer 42, which was prepared according to Example 28.

Isolated compound: 0.10 g (45%); mp: 186-188° C.; $[\alpha]_D^{20}=+18$ (c=0.25, MeOH); IR=3310, 2926, 1692, 1645, 1557, 1182 cm$^{-1}$. Anal. Calcd. for $C_{26}H_{38}N_2O_5$ (458.59): C, 68.10; H, 8.35; N, 6.11. Found: C, 68.39; H, 8.05; N, 6.28. $^1$H NMR (CDCl$_3$) δ (ppm): 0.93 (3H, s), 1.21 (3H, t, J=7.1 Hz), 1.22 (3H, s), 1.26 (9H, s), 1.31 (1H, d, H-4, J=11.1 Hz), 1.94-2.18 (5H, m), 2.29 (1H, m), 3.14 (2H, ddd, J=45.3, 14.1, 6.0 Hz), 4.13 (2H, dd, J=14.1, 7.1 Hz), 4.23-4.32 (1H, m), 4.66 (1H, br s, NH), 4.81-4.91 (1H, m), 6.89 (1H, br s, NH), 7.09-7.30 (5H, m). $^{13}$C NMR (CDCl$_3$) δ (ppm): 14.8, 20.1, 23.4, 27.2, 29.0, 29.4, 30.0, 32.6, 38.5, 40.3, 43.7, 47.2, 54.3, 62.0, 80.3, 127.5, 129.0, 130.0, 137.0, 156.0, 172.6, 174.1.

Example 35

(1R,2R,3S,5R)-1-(3-Ethoxycarbonyl-6,6-Dimethyl-bicyclo[3.1.1]Heptan-2-yl)-3-(3-Methoxyphenyl)-Thiourea (Compound 44) (Scheme 9)

0.086 g (0.52 mmol) of 3-methoxyphenyl isothiocyanate was added to a solution of 0.100 g (0.47 mmol) of ethyl (1R,2R,3S,5R)-2-amino-6,6-dimethylbicyclo[3.1.1]heptan-3-carboxylate 15 (prepared according to Example 7) in 10 ml of toluene. After stirring for 12 h at room temperature (the reaction was monitored by means of TLC), the solution was evaporated and crude product was crystallized and washed with n-hexane.

Isolated compound: 0.154 g (87%); mp: 132-135° C.; $[\alpha]_D^{20}=+10$ (c=0.25, MeOH); IR=3315, 3196, 2914, 1711, 1518, 1192, 702 cm$^{-1}$. Anal. Calcd. for $C_{20}H_{28}N_2O_3S$ (376.51): C, 63.80; H, 7.50; N, 7.44. Found: C, 63.61; H, 7.75; N, 7.32. $^1$H NMR (CDCl$_3$) δ (ppm): 0.95 (3H, s), 1.23 (3H, s), 1.23 (3H, t, J=7.1 Hz), 1.47 (1H, d, J=11.1 Hz), 1.91-2.21 (5H, m), 3.45 (1H, dt, J=11.1, 4.0 Hz), 3.82 (3H, s, OMe), 4.02-4.08 (2H, ddd, J=14.1, 7.0, 4.0 Hz, CH$_2$-CH$_3$), 5.31 (1H, t, J=10.1 Hz), 6.72 (1H, br s), 6.73 (1H, d, J=7.0 Hz), 6.81 (1H, d, J=7.1 Hz), 7.31 (1H, t, J=8.1 Hz), 7.78 (1H, br s). $^{13}$C NMR (CDCl$_3$) δ (ppm): 14.8, 20.9, 25.6, 26.8, 30.0, 38.0, 40.0, 40.2, 46.2, 54.6, 56.1, 61.6, 110.6, 112.7, 113.6, 117.1, 131.5, 137.1, 160.5 176.2.

Example 36

(1S,2S,3R,5S)-1-(3-Ethoxycarbonyl-6,6-Dimethylbi-cyclo[3.1.1]Heptan-2-yl)-3-(3-Methoxyphenyl)-Thiourea (Compound 54) (Scheme 11)

The synthesis of 1S,2S,3R,5S enantiomer 54 was accomplished by analogy with Example 35, starting from 1S,2S,3R,5S enantiomer amino ester 34, which was prepared according to Example 8; all the spectroscopic data and mp were similar to those for 1R,2R,3S,5R enantiomer 44.

Isolated compound: 0.154 g (87%); mp: 133-134° C.; $[\alpha]_D^{20}=-6$ (c=0.25, MeOH).

Example 37

(1R,2R,3S,5R)-1-(3-Ethoxycarbonyl-6,6-Dimethyl-bicyclo[3.1.1]Heptan-2-yl)-3-(4-Chlorophenyl)-Urea (Compound 45) (Scheme 9)

The synthesis of urea derivative 45 was accomplished by analogy with Example 35, starting from 0.100 g (0.47 mmol) of ethyl (1R,2R,3S,5R)-2-amino-6,6-dimethylbicyclo-[3.1.1]heptan-3-carboxylate 15 (prepared according to Example 7) and 0.079 g (0.52 mmol) of 4-chlorophenyl isocyanate.

Isolated compound: 0.153 g (89%); mp: 170-171° C.; $[\alpha]_D^{20}=+14$ (c=0.25, MeOH); IR=3318, 2948, 1725, 1654, 1562, 1493, 1174 cm$^{-1}$. Anal. Calcd. for $C_{19}H_{25}ClN_2O_3$ (364.87): C, 62.54; H, 6.91; N, 7.68. Found: C, 62.35; H, 7.28; N, 7.43. $^1$H NMR (CDCl$_3$) δ (ppm): 0.93 (3H, s), 1.20 (3H, t, J=7.1 Hz), 1.23 (3H, s), 1.49 (1H, d, J=10.1 Hz), 1.92-2.21 (5H, m), 3.31-3.47 (1H, m), 4.08 (2H, dd, J=14.1, 7.1 Hz), 4.73 (1H, t, J=9.1 Hz), 5.65 (1H, br s), 7.09 (1H, br s), 7.25 (4H, dd, J=18.1, 9.1 Hz). $^{13}$C NMR (CDCl$_3$) δ (ppm): 14.8, 21.0, 25.9, 26.9, 29.5, 39.4, 39.5, 40.1, 47.4, 48.8, 61.7, 121.6, 128.7, 129.8, 138.4, 155.2, 178.0.

Example 38

(1R,2R,3S,5R)-1-(3-Ethoxycarbonyl-6,6-Dimethyl-bicyclo[3.1.1]Heptan-2-yl)-3-(3,4-Dimethoxyphe-nylethyl)-Thiourea (Compound 46) (Scheme 9)

The synthesis of thiourea derivative 46 was accomplished by analogy with Example 35, starting from 0.10 g (0.47 mmol) of ethyl (1R,2R,3S,5R)-2-amino-6,6-dimethylbicyclo [3.1.1]heptan-3-carboxylate 15 (prepared according to Example 7) and 0.085 g (0.52 mmol) of 3,4-dimethoxyphenylethyl isothiocyanate.

Isolated compound: 0.125 g (61%); mp: 125-126° C.; $[\alpha]_D^{20}=+20$ (c=0.25, MeOH); IR=3357, 2936, 1723, 1514, 1260, 1156, 1027, 800 cm$^{-1}$. Anal. Calcd. for $C_{23}H_{34}N_2O_4S$ (434.59): C, 63.56; H, 7.89; N, 6.45. Found: C, 63.77; H, 7.59; N, 6.61. $^1$H NMR (CDCl$_3$) δ (ppm): 0.93 (3H, s), 1.24 (3H, s), 1.24 (3H, t, J=7.1 Hz), 1.55 (1H, d, H-4, J=10.4 Hz), 1.95-2.20 (5H, m), 2.80 (2H, t, J=6.9 Hz), 3.36 (1H, dt, J=6.9, 2.6 Hz), 3.46-3.61 (2H, m), 3.86 (3H, s), 3.88 (3H, s), 4.00-4.14 (2H, m), 5.12 (1H, br s), 5.91 (1H, br s), 6.59 (1H, br s), 6.74-6.82 (3H, m). $^{13}$C NMR (CDCl$_3$) δ (ppm): 14.8, 20.9, 25.5, 26.8, 30.0, 35.5, 38.0, 39.9, 40.1, 45.6, 46.5, 53.5, 56.6, 61.7, 112.2, 112.6, 121.4, 130.9, 148.6, 149.9, 151.9, 177.5.

Example 39

(1R,2R,3S,5R)-1-Benzyl-1-(3-Ethoxycarbonyl-6,6-Dimethylbicyclo[3.1.1]Heptan-2-yl)-3-(3-Methoxyphenyl)-Thiourea (Compound 47) (Scheme 9)

The synthesis of thiourea derivative 47 was accomplished by analogy with Example 35, starting from 0.142 g (0.47 mmol) of 1R,2R,3S,5R N-benzyl amino ester 20 (prepared according to Example 16) and 0.086 g (0.52 mmol) of 3-methoxyphenyl isothiocyanate.

Isolated compound: 0.148 g (68%); mp: 109-112° C.; $[\alpha]_D^{20}$=−4 (c=0.25, MeOH); IR=3346, 2898, 1713, 1597, 1493, 1186, 1032, 850 cm$^{-1}$. Anal. Calcd. for $C_{27}H_{34}N_2O_3S$ (466.64): C, 69.50; H, 7.34; N, 6.00. Found: C, 69.61; H, 7.11; N, 6,32. $^1$H NMR (CDCl$_3$) δ (ppm): 0.99 (3H, s), 1.23 (3H, s), 1.31 (3H, t, J=7.1 Hz), 1.91-2.11 (4H, m), 2.22 (1H, d, H-4, J=11.1 Hz), 2.27-2.37 (1H, m), 3.72 (3H, s), 4.02 (1H, t, J=7.1 Hz), 4.17 (2H, dd, J=14.1, 7.1 Hz), 4.53-4.68 (1H, m), 4.93 (1H, d, J=18.1 Hz), 6.03 (1H, br s), 6.54 (1H, d, J=8.1 Hz), 6.61-6.73 (2H, m), 6.88 (1H, br s, NH), 7.11 (1H, t, J=7.1 Hz), 7.22-7.46 (5H, m). $^{13}$C NMR (CDCl$_3$) δ (ppm): 15.1, 21.2, 26.9, 27.2, 29.1, 38.1, 39.4, 41.5 44.5, 51.2, 55.9, 60.6, 61.6, 111.9, 118.3, 125.4, 126.5, 128.3, 128.7, 129.8, 130.0, 136.1, 140.5, 160.2, 176.7.

Example 40

(1R,2R,3S,5R)-1-Benzyl-1-(3-Ethoxycarbonyl-6,6-Dimethylbicyclo[3.1.1]Heptan-2-yl)-3-(4-Chlorophenyl)-Urea (Compound 48) (Scheme 9)

The synthesis of urea derivative 48 was accomplished by analogy with Example 35, starting from 0.142 g (0.47 mmol) of 1R,2R,3S,5R N-benzyl amino ester 20 (prepared according to Example 16) and 0.079 g (0.52 mmol) of 4-chlorophenyl isocyanate.

Isolated compound: 0.161 g (75%); mp: 202-205° C.; $[\alpha]_D^{20}$=+5 (c=0.25, MeOH); IR=3321, 2940, 1723, 1636, 1526, 1493, 1241, 1178, 828, 696 cm$^{-1}$. Anal. Calcd. for $C_{26}H_{31}ClN_2O_3$ (454.99): C, 68.63; H, 6.87; N, 6.16. Found: C, 68.35; H, 6.96; N, 5.93. $^1$H NMR (CDCl$_3$) δ (ppm): 0.94 (3H, s), 1.19 (3H, t, J=7.1 Hz), 1.23 (3H, s), 1.90-2.18 (4H, m), 2.21 (1H, d, J=10.1 Hz), 2.27-2.33 (1H, m), 3.65 (1H, dt, J=10.1, 3.0 Hz), 4.10 (2H, ddd, J=14.1, 7.1, 2.0 Hz), 4.31 (1H, d, J=18.1 Hz), 4.64 (1H, d, J=18.1 Hz), 5.10 (1H, d, J=9.1 Hz), 6.11 (1H, br s, NH), 7.00 (2H, d, J=8.1 Hz), 7.12 (2H, d, J=8.1 Hz), 7.22-7.42 (5H, m). $^{13}$C NMR (CDCl$_3$) δ (ppm): 14.9, 20.9, 26.8, 27.1, 29.0, 39.3, 39.5, 41.2, 44.3, 48.6, 55.6, 61.7, 121.5, 126.7, 128.5, 128.6, 129.3, 130.0, 138.3, 138.6, 156.1, 177.6.

Example 41

(1R,2R,3R,5R)-1-(3-Ethoxycarbonyl-6,6-Dimethylbicyclo[3.1.1]Heptan-2-yl)-3-(3-Methoxyphenyl)-Thiourea (Compound 49) (Scheme 10)

The synthesis of thiourea derivative 49 was accomplished by analogy with Example 35, starting from 0.10 g (0.47 mmol) of ethyl (1R,2R,3R,5R)-2-amino-6,6-dimethylbicyclo[3.1.1]heptan-3-carboxylate 26 (prepared according to Example 23) and 0.086 g (0.52 mmol) of 3-methoxyphenyl isothiocyanate.

Isolated compound: 0.145 g (82%); mp: 118-120° C.; $[\alpha]_D^{20}$=−86 (c=0.25, MeOH); IR=3344, 3158, 2918, 1731, 1540, 1148, 694 cm$^{-1}$. Anal. Calcd. for $C_{20}H_{28}N_2O_3S$ (376.51): C, 63.80; H, 7.50; N, 7.44. Found: C, 63.69; H, 7.63; N, 7.21. $^1$H NMR (CDCl$_3$) δ (ppm): 0.96 (3H, s), 1.25 (3H, s), 1.30 (3H, t, J=7.1 Hz), 1.47 (1H, br s), 1.91-2.23 (5H, m,), 2.6 (1H, br s), 3.81 (3H, s), 4.23 (2H, dd, J=14.1, 7.0), 5.11 (1H, br s), 6.25 (1H, br s), 6.72-7.01 (3H, m), 7.30 (1H, t, J=8.1 Hz), 7.81 (1H, br s). $^{13}$C NMR (CDCl$_3$) δ (ppm): 14.9, 20.1, 24.0, 27.0, 27.9, 29.2, 40.1, 42.1, 46.3, 56.1, 62.1, 110.5, 112.5, 116.9, 130.5, 160.8, 180.3.

Example 42

(1S,2S,3S,5S)-1-(3-Ethoxycarbonyl-6,6-Dimethylbicyclo[3.1.1]Heptan-2-yl)-3-(3-Methoxyphenyl)-Thiourea (Compound 55) (Scheme 12)

The synthesis of 1S,2S,3S,5S enantiomer 55 was accomplished by analogy with Example 35, starting from 0.100 g (0.47 mmol) of 1S,2S,3S,5S enantiomer amino ester 39, which was prepared according to Example 24; all the spectroscopic data and mp were similar to those for 1R,2R,3R,5R enantiomer 49.

Isolated compound: 0.145 g (82%); mp: 120-122° C.; $[\alpha]_D^{20}$=+22 (c=0.25, MeOH).

Example 43

(1R,2R,3R,5R)-1-(3-Ethoxycarbonyl-6,6-Dimethylbicyclo[3.1.1]Heptan-2-yl)-3-(4-Chlorophenyl)-Urea (Compound 50) (Scheme 10)

The synthesis of urea derivative 48 was accomplished by analogy with Example 35, starting from 0.10 g (0.47 mmol) of ethyl (1R,2R,3R,5R)-2-amino-6,6-dimethylbicyclo[3.1.1]heptan-3-carboxylate 26 (prepared according to Example 23) and 0.079 g (0.52 mmol) of 4-chlorophenyl isocyanate.

Isolated compound: 0.133 g (78%); mp: 167-169° C.; $[\alpha]_D^{20}$=−38 (c=0.25, MeOH); IR=3328, 2926, 1727, 1654, 1558, 1493, 1156, 830 cm$^{-1}$. Anal. Calcd. for $C_{19}H_{25}ClN_2O_3$ (364.87): C, 62.54; H, 6.91; N, 7.68. Found: C, 62.75; H, 6.78; N, 7.53. $^1$H NMR (CDCl$_3$) δ (ppm): 0.90 (3H, s), 1.23 (3H, s), 1.27 (3H, t, J=7.1 Hz), 1.37 (1H, d, H-4, J=10.1 Hz), 1.86-2.08 (3H, m), 2.13-2.28 (2H, m,), 2.64-2.74 (1H, m), 4.21 (2H, dd, J=14.1, 7.1 Hz), 4.37 (1H, d, J=8.1 Hz), 7.20 (1H, d, J=8.1 Hz), 7.32 (1H, d, J=8.1 Hz), 7.91 (1H, br s, NH). $^{13}$C NMR (CDCl$_3$) δ (ppm): 14.8, 20.2, 24.1, 27.0, 28.7, 40.2, 40.5, 43.4, 47.2, 52.1, 62.1, 121.1, 127.9, 129.5, 137.7, 155.3, 176.8.

Example 44

(1S,2S,3S,5S)-1-(3-Ethoxycarbonyl-6,6-Dimethylbicyclo[3.1.1]Heptan-2-yl)-3-(4-Chlorophenyl)-Urea (Compound 56) (Scheme 12)

The synthesis of 1S,2S,3S,5S enantiomer 56 was accomplished by analogy with Example 35, starting from 0.10 g (0.47 mmol) of ethyl 1S,2S,3S,5S-2-amino-6,6-dimethylbicyclo[3.1.1]heptan-3-carboxylate enantiomer amino ester 39, which was prepared according to Example 24, and 0.079 g (0.52 mmol) of 4-chlorophenyl isocyanate; all the spectroscopic data and mp were similar to those for 1R,2R,3R,5R enantiomer 50.

Example 45

(1R,2R,3R,5R)-1-(3-Ethoxycarbonyl-6,6-Dimethyl-bicyclo[3.1.1]Heptan-2-yl)-3-(3,4-Dimethoxyphenyl-Ethyl)-Thiourea (Compound 51) (Scheme 10)

The synthesis of thiourea derivative 51 was accomplished by analogy with Example 35, starting from 0.10 g (0.47 mmol) of ethyl (1R,2R,3R,5R)-2-amino-6,6-dimethylbicyclo[3.1.1]heptan-3-carboxylate 26 (prepared according to Example 23) and 0.085 g (0.52 mmol) of 3,4-dimethoxyphenylethyl isothiocyanate with that modification, that the oily crude product was purified by flash chromatography on a silica gel column (toluene:ethanol=9:1) resulting in compound 51.

Isolated compound: 0.120 g (59%); oil; $[\alpha]_D^{20}$=−32 (c=0.25, MeOH); IR=3350, 2932, 1729, 1514, 1261, 1025, 806 cm$^{-1}$. Anal. Calcd. for $C_{23}H_{34}N_2O_4S$ (434.59): C, 63.56; H, 7.89; N, 6.45. Found: C, 63.65; H, 7.61; N, 6.73. $^1$H NMR (CDCl$_3$) δ (ppm): 0.78 (3H, s), 1.22 (3H, s), 1.26 (3H, t, J=7.1 Hz), 1.37 (1H, d, J=11.1 Hz), 1.77 (1H, dd, J=10.1, 13.0), 1.96-2.01 (2H, m), 2.16-2.34 (2H, m), 2.67-2.97 (3H, m), 3.76-3.87 (8H, m), 4.10-4.25 (3H, m), 6.05 (1H, d, J=9.1 Hz), 6.78-6.83 (3H, m), 7.10 (1H, br s, NH). $^{13}$C NMR (CDCl$_3$) δ (ppm): 14.8, 20.2, 24.4, 26.8, 29.1, 35.3, 40.1, 40.2, 42.4, 46.6, 47.6, 53.9, 56.5, 56.6, 62.2, 112.0, 112.8, 121.4, 128.8, 132.1, 137.6, 148.7, 176.7.

Example 46

(1R,2R,3R,5R)-1-Benzyl-1-(3-Ethoxycarbonyl-6,6-Dimethylbicyclo[3.1.1]-Heptan-2-yl)-3-(3-Methoxyphenyl)-Thiourea (Compound 52) (Scheme 10)

The synthesis of thiourea derivative 52 was accomplished by analogy with Example 35, starting from 0.142 g (0.47 mmol) of 1R,2R,3R,5R N-benzyl amino ester 27 (prepared according to Example 25) and 0.086 g (0.52 mmol) of 3-methoxyphenyl isothiocyanate.

Isolated compound: 0.140 g (64%); mp: 110-111° C.; $[\alpha]_D^{20}$=+2 (c=0.25, MeOH); IR=3340, 2936, 1710, 1610, 1543, 1496, 1282, 1057 cm$^{-1}$. Anal. Calcd. for $C_{27}H_{34}N_2O_3S$ (466.64): C, 69.50; H, 7.34; N, 6.00. Found: C, 69.41; H, 7.53; N, 6.12. $^1$H NMR (CDCl$_3$) δ (ppm): 0.90 (3H, s), 1.26 (3H, s), 1.27 (3H, t, J=7.1 Hz), 1.61 (1H, d, J=10.7 Hz), 1.76 (1H, dd, J=13.2, 10.1 Hz), 1.90-1.93 (1H, m), 2.09-2.16 (2H, m), 2.34-2.39 (1H, m), 2.86 (1H, dd, J=19.7, 9.8 Hz), 3.82 (3H, s), 4.13-4.30 (2H, m), 4.57 (1H, d, J=16.8 Hz), 5.37 (1H, d, J=9.7 Hz), 6.69 (1H, dd, J=10.3, 2.1 Hz), 7.06 (1H, d, J=7.8 Hz), 7.21-7.31 (7H, m), 9.52 (1H, br s). $^{13}$C NMR (CDCl$_3$) δ (ppm): 14.8, 20.2, 26.0, 27.2, 29.0, 39.1, 39.4, 42.0, 46.6, 50.0, 56.0, 59.1, 62.4, 110.7, 111.0, 117.1, 126.8, 127.6, 129.2, 129.7, 142.6, 185.4.

Example 47

(1R,2R,3R,5R)-1-Benzyl-1-(3-Ethoxycarbonyl-6,6-Dimethylbicyclo[3.1.1]-Heptan-2-yl)-3-(4-Chlorophenyl)-Urea (Compound 53) (Scheme 10)

The synthesis of urea derivative 53 was accomplished by analogy with Example 35, starting from 0.142 g (0.47 mmol) of 1R,2R,3R,5R N-benzyl amino ester 27 (prepared according to Example 25) and 0.079 g (0.52 mmol) of 4-chlorophenyl isocyanate with that modification, that the oily crude product was purified by flash chromatography on a silica gel column (toluene:ethanol=9:1) resulting in compound 53.

Isolated compound: 0.150 g (70%); oil; $[\alpha]_D^{20}$=+4 (c=0.25, MeOH); IR=3332, 2926, 1704, 1676, 1595, 1496, 1211, 830 cm$^{-1}$. Anal. Calcd. for $C_{26}H_{31}ClN_2O_3$ (454.99): C, 68.63; H, 6.87; N, 6.16. Found: C, 68.75; H, 6.63; N, 6.41. $^1$H NMR (CDCl$_3$) δ (ppm): 0.92 (3H, s), 1.23 (3H, s), 1.26 (3H, t, J=7.1 Hz), 1.57 (1H, d, J=10.7 Hz), 1.76 (1H, dd, J=13.2, 10.1 Hz), 1.89-1.93 (1H, m), 2.02 (1H, t, J=5.3 Hz), 2.11-2.18 (1H, m), 2.28-2.35 (1H, m), 2.86 (1H, dd, J=19.5, 9.7 Hz), 4.14-4.30 (3H, m), 4.80 (1H, d, J=9.7 Hz), 4.87 (1H, d, J=16.6 Hz), 7.17-7.39 (9H, m), 8.53 (1H, br s). $^{13}$C NMR (CDCl$_3$) δ (ppm): 14.9, 20.2, 26.0, 27.2, 29.0, 39.4, 39.7, 41.7, 45.7, 46.3, 56.2, 62.2, 121.3, 127.0, 127.6, 127.7, 129.2, 129.3, 139.4, 140.3, 157.0, 177.9.

In the enclosed FIG. 2 relating to the Summarizing Formula Table the meanings of substituents X and Y are given by reference to the individual Examples and to the numbers of the compounds prepared according to the Examples.

Biological Assays

The following examinations carried out in connection with the multidrug resistance reversing effect of the compounds according to the invention prove that the novel compounds are modulators of the mdr1 gene transfected into the mouse lymphoma cell line.

Cell Cultures

L5178 mouse T-cell lymphoma cells were transfected with pHa MDR1/A retrovirus, by the method as described by J. L. Weaver [J. L. Weaver, G. Szabó, P. S. Pine, M. M. Gottesmann, S. Goldenberg and A. Aszalos: The effect of ion channel blockers, immunosuppressive agents and other drugs on the activity of the multidrug transporter. *Int. J. Cancer* 54, 456-61 (1993)]. Mdr-1-expressing cell lines were selected by culturing the transfected cells with 60 ng/mL of colchicine to maintain the expression of the MDR phenotype. L5178 (parent) mouse T-cell lymphoma cells and the human mdr1 transfected subline were cultured in McCoy's 5A medium supplemented with 10% by mass of heath-inactivated horce serum, L-glutamine and antibiotics. Both cell lines were cultured at 37° C. The mouse lymphoma cell line was maintained in a 5% CO$_2$ atmosphere.

Method

Reversal of Multidrug Resistance

As pre-assay, the concentrations inhibiting 50% of cell proliferation were determined. Based on the ID$_{50}$ values indicating the antiproliferative effect of the tested compounds, they proved to be non-cytotoxic under the test conditions; consequently the measurements could be performed.

The assays were carried out by the method as described by J. Molnár et al. [J. Molnár, I. Mucsi, J. Nacsa, A. Hevér, N. Gyémánt, K. Ugocsai, P. Hegyes, S. Kiessig, D. Gaal, H. Lage and A. Varga: New silicon compounds as resistance modifiers against multidrug-resistant cells. *Anticancer Research* 24, 865-71 (2004)]. The cell density was set to a value of $2\times10^6$/mL, then the cells were resuspended in a serum-free McCoy's 5A medium and divided in aliquots of 0.5 mL in Eppendorf centrifuge tubes. The tested compounds were added in different concentrations to different volumes (2.0-20.0 μL) of 1.0-10.0 mg/mL stock solutions and the samples were incubated for 10 minutes at room temperature. Thereafter 10 μL (5.2 μM final concentration) of indicator rhodamine 123 were added to each sample [D. Kessel: Exploring multidrug resistance using rhodamine 1223, *Cancer Commun.* 145-149 (1989)] and the cells were incubated for further 20 minutes at 37° C., then washed twice with phosphate buffer and resuspended in 0.5 ml of phosphate buffer for analysis. The fluorescence of the cell population was measured with a Beckton Dickinson FACScan flow cytometer. Verapamil was used as a positive control in the rhodamine 123 experiments [M. M. Cornwell, I. Pastan and M. M. Gottesmann: Certain calcium channel blockers bind specifically to multidrug resistant human KB carcinoma membrane vesicles and inhibit drug binding t P-glycoprotein. *J. Biol. Chem.* 262, 2166-70 (1987)]. The percentage value of the mean fluorescence intensity was calculated for the treated MDR and for the parental cell lines as compared with the values obtained with the untreated cells. The activity ratio (R) was calculated on the basis of the measured fluorescence values by the following equation:

$$R = \frac{MDR \text{ treated}/MDR \text{ control}}{\text{parental treated}/\text{parental control}}$$

Results

Multidrug Resistance Reversing Effect

In our assays the compounds were tested in two concentrations (4 and 40 μg/mL), wherein Verapamil was used as positive in vitro control (Tables 2 and 3). A significant dose-dependent effect was observed with the compounds of formulas 44, 46, 47, 49, 50, 51 and 56: in higher concentrations they gave multiple values of the fluorescence activity of the positive control Verapamil measured at the concentration used.

Compounds of formulas 47 and 52 showed even at lower concentrations a considerable multidrug resistance reversing effect; at higher concentrations similar fluorescence activity values were measured (Table 3), indicating saturation.

The effect of compound of formula 47 was separately tested in a concentration series (0.04, 0.08, 0.4, 0.8 and 4 μg/mL). Dose-dependence was observed: it can be noted that already a concentration of 0.4 μg/mL of this compound is sufficient for exerting a significant P-glycoprotein-inhibiting effect (Table 4).

TABLE 2

| Number of formula of the compound | μg/ml | R | Vrel |
|---|---|---|---|
| Verapamil | 10 | 4.92 | 1.00 |
| 46 | 4 | 4.02 | 0.82 |
|  | 40 | 21.92 | 4.46 |
| 51 | 4 | 13.29 | 2.70 |
|  | 40 | 49.02 | 9.96 |
| 44 | 4 | 2.02 | 0.41 |
|  | 40 | 22 | 4.47 |
| 49 | 4 | 2.77 | 0.56 |
|  | 40 | 28.07 | 5.71 |
| 54 | 4 | 2.37 | 0.48 |
|  | 40 | 26.35 | 5.36 |
| 55 | 4 | 3.07 | 0.62 |
|  | 40 | 11.99 | 2.44 |
| 45 | 4 | 7.46 | 1.52 |
|  | 40 | 10.89 | 2.21 |
| 38 | 4 | 2.33 | 0.79 |
|  | 40 | 19.92 | 6.73 |

TABLE 3

| Number of formula of the compound | μg/ml | R | Vrel |
|---|---|---|---|
| Verapamil | 10 | 11.45 | 1.00 |
| 50 | 4 | 1.87 | 0.16 |
|  | 40 | 42.58 | 3.70 |

TABLE 3-continued

| Number of formula of the compound | μg/ml | R | Vrel |
|---|---|---|---|
| 56 | 4 | 1.57 | 0.14 |
|  | 40 | 39.39 | 3.43 |
| 47 | 4 | 34.76 | 3.02 |
|  | 40 | 35.35 | 3.07 |
| 52 | 4 | 21.87 | 1.90 |
|  | 40 | 24.44 | 2.13 |
| 41 | 4 | 0.86 | 0.07 |
|  | 40 | 1.25 | 0.11 |
| 17 | 4 | 23.1 | 1.58 |
|  | 40 | 94.24 | 6.45 |

R = ratio of fluorescence and activity
Vrel = effect related to Verapamil

TABLE 4

| Tested compound | c (μg/ml) | R |
|---|---|---|
| Verapamil | 10 | 21.37 |
| Compound of formula 47 | 4 | 35.20 |
|  | 0.8 | 7.16 |
|  | 0.4 | 6.03 |
|  | 0.08 | 1.60 |
|  | 0.04 | 1.44 |

What is claimed is:

1. A compound comprising a chiral cyclic 2-amino-6,6-dimethyl-bicyclo[3.1.1]heptane-3-carboxylic acid derivative of general formula (I)

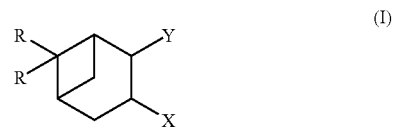

wherein

R is $C_{1-4}$ Alk;

X is —COOH, —CONH$_2$, —CONH(C$_{1-4}$ Alk), —CON(C$_{1-4}$ Alk)$_2$, —COO(C$_{1-4}$ Alk), —COPhe-O—(C$_{1-4}$ Alk) or —CH$_2$OH;

Y is —NH$_2$, —NHBoc, —NHFmoc, —NH(C$_{1-4}$ Alk), —N(C$_{1-4}$ Alk)$_2$, —NHCH$_2$Ph, or Ar—NH—C(=X$^0$)—N(R$^0$)—, wherein Ar is a phenyl group substituted by one or two C$_{1-4}$ alkoxy group(s) or by one halogen, X$^0$ is O or S, and R$^0$ is hydrogen or benzyl; and X+Y is —CONH— or —CON(Boc)-;

with the proviso that if X is —COOH, then Y is not —NH$_2$ and their salts formed with pharmaceutically acceptable acids or bases.

2. The compound as claimed in claim 1, selected from the group consisting of:

(1R,2R,5S,7R)-N-tert-butoxycarbonyl-8,8-dimethyl-3-aza-tricyclo[5.1.1.0$^{2,5}$]nonane-4-one (compound 11), (1R,2R,3R,5R)-2-(9H-fluoren-9-yl-methoxycarbonylamino)-6,6-dimethyl-bicyclo[3.1.1]heptane-3-carboxylic acid (compound 30), (1R,2R,3S,5R)-1-(3-ethoxycarbonyl-6,6-dimethyl-bicyclo-[3.1.1]heptane-2-yl)-3-(3-methoxyphenyl)-thiourea (compound 44), (1R,2R,3S,5R)-1-(3-ethoxycarbonyl-6,6-dimethyl-bicyclo[3.1.1]heptane-2-yl)-3-(3,4-dimethoxy-phenyl-ethyl)-thiourea (compound 46), (1R,2R,3S,5R)-1-benzyl-1-(3-ethoxycarbonyl-6,6-dimethyl-bicyclo[3.1.1]heptane-2-yl)-3-(3-methoxyphenyl)-thiourea (compound 47), (1R,2R,3R,5R)-1-(3-ethoxycarbonyl-6,6-dimethyl-bicyclo[3.1.1]heptane-2-yl)-3-(3-methoxyphenyl)-thiourea (compound 49), (1R,2R,3R,5R)-1-(3-ethoxycarbonyl-6,6-dimethyl-bicyclo-[3.1.1]heptane-2-yl)-3-(4-chlorophenyl)-urea (compound 50), (1R,2R,3R,5R)-1-(3-ethoxycarbonyl-6,6-dimethyl-bicyclo-[3.1.1]heptane-2-yl)-3-(3,4-dimethoxyphenyl-ethyl)-thiourea (compound 51), (1R,2R,3R,5R)-1-benzyl-1-(3-ethoxycarbonyl-6,6-dimethyl-bicyclo[3.1.1]heptane-2-yl)-3-(3-methoxyphenyl)-thiourea (compound 52), and (1S,2S,3S,5S)-1-(3-ethoxycarbonyl-6,6-dimethyl-bicyclo-[3.1.1]heptane-2-yl)-3-(4-chlorophenyl)-urea (compound 56).

3. A compound as claimed in claim 1, wherein the compound is derived from an intermediate compound selected from the group consisting of:

(1R,2R,3S,5R)-2-Amino-6,6-dimethyl-bicyclo[3.1.1]heptane-3-carboxylic acid (compound 6), (1S,2S,3R,5S)-2-Amino-6,6-dimethyl-bicyclo[3.1.1]heptane-3-carboxylic acid (compound 7), (1R,2R,3R,5R)-2-Amino-6,6-dimethyl-bicyclo[3.1.1]heptane-3-carboxylic acid (compound 8), and (1S,2S,3S,5S)-2-Amino-6,6-dimethyl-bicyclo[3.1.1]heptane-3-carboxylic acid (compound 9).

4. A pharmaceutical composition comprising one or more compounds of general formula (I) as active agent and/or the salts thereof as claimed in claim 1 and inert pharmaceutical carriers and/or auxiliary agents.

5. A method for preparing pharmaceutical compositions, comprising mixing one or more compound(s) of general formula (I) and/or the salts thereof as claimed in claim 1 with an inert pharmaceutical carrier and/or auxiliary agents.

6. A method for reversing multi-drug resistance involving efflux-pump activity in tumor cells, comprising administering an effective amount of the composition of claim 4 to a subject in need of such treatment.

7. A method for reversing multi-drug resistance involving p-glycoprotein activity in tumor cells, comprising administering an effective amount of the composition of claim 4 to a subject in need of such treatment.

8. The method of claim 7, wherein the cancer is lymphoma.

9. A method for suppressing efflux-pump activity in cancer cells of a subject, comprising administering an effective amount of the composition of claim 4 to the subject.

10. A method for suppressing efflux-pump activity in mammalian cells in vitro, comprising culturing the cells in the presence of an effective amount of the compound of claim 1.

11. A method of producing the compound of claim 1, comprising derivatizing an intermediate compound selected from the group consisting of:

(1R,2R,3S,5R)-2-Amino-6,6-dimethyl-bicyclo[3.1.1]-heptane-3-carboxylic acid (compound 6), (1S,2S,3R,5S)-2-Amino-6,6-dimethyl-bicyclo[3.1.1]-heptane-3-carboxylic acid (compound 7), (1R,2R,3R,5R)-2-Amino-6,6-dimethyl-bicyclo[3.1.1]-heptane-3-carboxylic acid (compound 8), and (1S,2S,3S,5S)-2-Amino-6,6-dimethyl-bicyclo[3.1.1]-heptane-3-carboxylic acid (compound 9).

* * * * *